United States Patent
Abbott et al.

(10) Patent No.: US 9,863,923 B2
(45) Date of Patent: Jan. 9, 2018

(54) METHOD OF DETECTION OF VOLATILE ORGANIC COMPOUNDS USING LIQUID CRYSTALS THAT FORM A BLUE PHASE; AND DEVICE FOR STABILIZATION AND THICKNESS CONTROL OF LIQUID CRYSTAL FILMS

(71) Applicant: Wisconsin Alumni Research Foundation, Madison, WI (US)

(72) Inventors: Nicholas L. Abbott, Madison, WI (US); Marco Antonio Bedolla Pantoja, Madison, WI (US); Xiaoguang Wang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/971,014

(22) Filed: Dec. 16, 2015

(65) Prior Publication Data

US 2016/0178588 A1    Jun. 23, 2016

Related U.S. Application Data

(60) Provisional application No. 62/094,520, filed on Dec. 19, 2014.

(51) Int. Cl.
*C09K 19/02* (2006.01)
*G01N 33/00* (2006.01)
(Continued)

(52) U.S. Cl.
CPC ..... *G01N 33/0047* (2013.01); *C09K 19/0275* (2013.01); *C09K 19/2021* (2013.01);
(Continued)

(58) Field of Classification Search
CPC ...................................................... C09K 19/18
See application file for complete search history.

(56) References Cited

U.S. PATENT DOCUMENTS

2011/0234944 A1*  9/2011  Powers ............... C09K 19/544
                                                          349/86
2014/0302612 A1   10/2014  Shenoy

FOREIGN PATENT DOCUMENTS

WO      2007/041570 A1    4/2007
WO      2010/126774 A1   11/2010
WO   WO 2010126774 A1 * 11/2010 ............ G01N 21/21

OTHER PUBLICATIONS

McCamley, Maureen K., et al., "Optical detection of sepsis markers using liquid crystal based biosensors," Optomechatronic Micro/Nano Devices and Components III: Oct. 8-10, 2007, Lausanne, Switzerland, vol. 6441, Feb. 8, 2007, pp. 64411Y-64411Y-8.

(Continued)

*Primary Examiner* — Chanceity Robinson
(74) *Attorney, Agent, or Firm* — Boyle Fredrickson S.C.

(57) ABSTRACT

Methods and compositions for detecting a targeted analyte, such as volatile organic compound (VOCs), are disclosed. Specifically, a cholesteric liquid crystal composition comprising a nematic liquid crystal and a chiral dopant transitions to a liquid crystal blue phase or undergoes other optical changes when in contact with a sample containing the analyte. The phase transition can be readily detected with the naked eye. The disclosed methods and compositions may be used in, for example, dosimeters for detecting analyte (e.g., VOC) exposure. Methods and compositions for producing arrays of liquid crystal thin films are also disclosed. The surface between the microwells in a microwell array is coated with a liquid-crystal-phobic material, such as a fluorinated polymer or a fluorinated silane, creating isolated microwell domains that are preferentially wetted by liquid (Continued)

crystal. Liquid crystal can be added to the microwell domains by simple techniques such as spin coating.

4 Claims, 30 Drawing Sheets
(24 of 30 Drawing Sheet(s) Filed in Color)

(51) Int. Cl.
    *C09K 19/36*     (2006.01)
    *G02F 1/1333*     (2006.01)
    *G02F 1/1341*     (2006.01)
    *C09K 19/20*     (2006.01)

(52) U.S. Cl.
    CPC ............ *C09K 19/36* (2013.01); *G02F 1/1341* (2013.01); *G02F 1/133377* (2013.01); *C09K 2219/17* (2013.01)

(56) References Cited

OTHER PUBLICATIONS

Drapp, B., et al. "The application of the phase transition in nematic liquid crystals for the optical detection of volatile organic compounds." Fresenius' journal of analytical chemistry 364.1-2 (1999): 121-127.

Chang, Chin-Kai, et al. "Optical detection of organic vapors using cholesteric liquid crystals." Applied Physics Letters 99.7 (2011): 073504.

Karatairi, Eva, et al. "Nanoparticle-induced widening of the temperature range of liquid-crystalline blue phases." Physical Review E 81.4 (2010): 041703.

Ravnik, Miha, et al. "Three-dimensional colloidal crystals in liquid crystalline blue phases." Proceedings of the National Academy of Sciences 108.13 (2011): 5188-5192.

Kasch, Nicholas, Ingo Dierking, and Michael Turner. "Stabilization of the liquid crystalline blue phase by the addition of short-chain polystyrene." Soft Matter Sep. 19, 2013: 4789-4793.

* cited by examiner

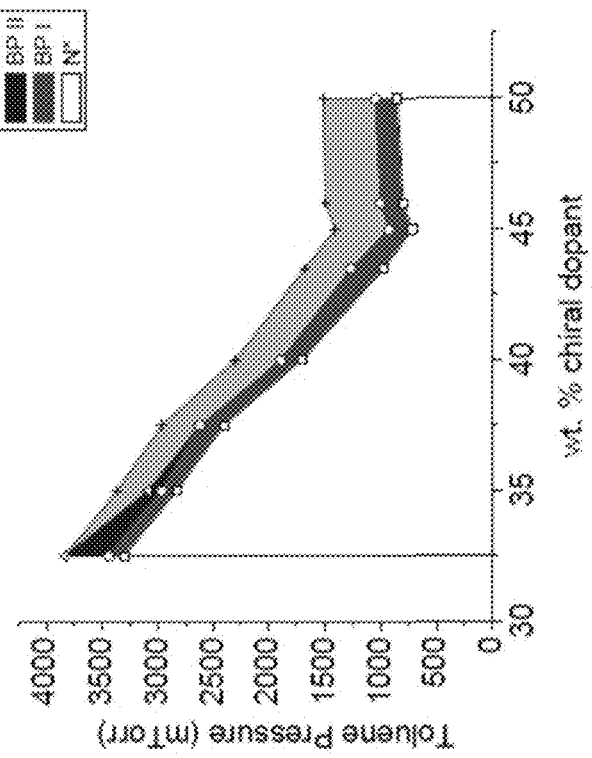
Fig. 3A:
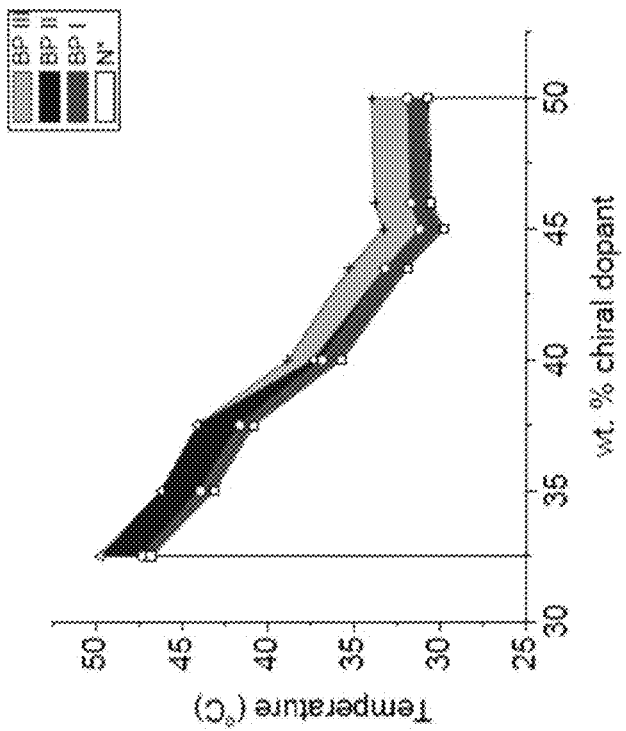
Fig. 3B:
Figs. 3A and 3B

METHOD OF DETECTION OF VOLATILE ORGANIC COMPOUNDS USING LIQUID CRYSTALS THAT FORM A BLUE PHASE; AND DEVICE FOR STABILIZATION AND THICKNESS CONTROL OF LIQUID CRYSTAL FILMS

CROSS-REFERENCE TO RELATED APPLICATION

This application claims of the benefit of U.S. provisional Application No. 62/094,520 filed on Dec. 19, 2015, which is incorporated by reference herein in its entirety.

STATEMENT REGARDING FEDERALLY SPONSORED RESEARCH

This invention was made with government support under 1121288 awarded by the National Science Foundation and W911NF-11-1-0251 and W91NF-10-1-0181 awarded by the US Army/ARO. The government has certain rights in the invention.

BACKGROUND

Volatile organic compounds (VOCs) are chemical species emitted by certain solids or liquids commonly used in industrial and household products, but many of them pose severe risks to human health and may form explosive mixtures in air. In particular, VOCs with aromatic moieties, such as benzene, styrene, toluene, and xylene, are considered carcinogenic, can cause adverse health effects upon short-term exposure, and form explosive mixtures in air at concentrations as low as 1 vol. % in air.[1-3] However, the lack of chemically reactive functionalities in these molecules means that they are difficult to detect using conventional electrochemical detection methods.

Commercial methods of detection of this type of VOCs often involve off-site analytical methods or centralized detection equipment, such as colorimetric detectors, photoionization detectors, or portable infrared spectroscopes. These methods of detection can be expensive, and they do not provide information about personal exposure monitoring. In many occupational settings, the local concentrations of VOCs to which a person is exposed might reach levels much higher than those being measured several feet away by centralized detection equipment.[4,5]

Accordingly, there is a need in the art for technologies that could be used to develop cheap, wearable devices for monitoring personal exposure to aromatic VOCs. In particular, there is a need for power-free devices that are able to detect local concentrations of VOCs and to retain a history of exposure to VOCs. Such devices could be used in, for example, occupational hygiene, chemical storage sites, and equipment for first-responders.

A problem associated with liquid crystal-based technology is that films of liquid crystal (LC) supported on a solid substrates tend to deform and dewet. Previous approaches aimed at stabilizing LC films having a thickness in the micrometer range include the use of metal grids, polyurethane microwells and micropillar arrays. In the case of the grids and the polyurethane wells, manual filling is tedious and not practical for manufacturing, and makes it difficult to precisely control the LC thickness. High density arrays of micropillars use capillary forces to stabilize LC films, but they generate significant distortions of the director that might influence the behavior of the LC and they are difficult to reproducibly fill. Moreover, it can be difficult to control the surface chemistry of the micropillar arrays. The LC also tends to dewet the micropillars at the edge of the array.

Accordingly, there is a need in the art for methods and devices that allow for precise control of thickness and control of the surface anchoring conditions of LC films disposed on surfaces.

BRIEF SUMMARY

In this disclosure, we first present a novel method to detect a target analyte, such as, but not limited to, volatile organic compounds (VOCs). The method uses a blue phase (BP)-forming liquid crystal composition (i.e., a cholesteric LC composition) containing a nematic liquid crystal and a chiral dopant. To date, such compositions have not been studied in the context of chemical sensing applications. By varying the amounts of the chiral dopant, and optionally, adding a non-volatile organic compound, such as pyrene, to the composition, we effectively promote the formation of disclination lines, and thus the transitioning of the composition to one of three distinct liquid crystal blue phases. Using these methods, we successfully and unexpectedly demonstrated that the cholesteric LC compositions can exhibit an optical response to toluene, an exemplary target analyte, at a concentration of below 200 ppm, which is the limit for human exposure over 8 hours, as established by the U.S. Occupational Safety & Health Administration. Furthermore, the relatively high viscosity of the cholesteric LC compositions used herein can be exploited to induce a hysteresis on the compositions upon target analyte exposure that provides a non-reversible marker for such exposure.

The mechanism of target analyte detection using BP LCs could pave the way for the development of power-free, wearable devices for detection of, for example, volatile organic compounds (VOCs) with unreactive chemical functionalities, such as aromatic compounds. The advantages of our detection method in comparison to other previously published methods are the following: (i) the LC composition does not require an alignment layer, (ii) the method does not require the use of light polarizers; (iii) the optical transition in the composition induced by the presence of VOCs can be observed with the naked eye; (iv) the sensitivity towards the target analyte can be easily modified by changing the concentration of the chiral dopant; (v) the sensitivity towards the target analyte can be easily modified through the addition of a non-volatile organic compound (a sensitizing agent); and (vi) the material can be easily processed in such a way that it retains a history of transient exposure to the target analyte.

Accordingly, in a first aspect, the disclosure encompasses a method for detecting a target analyte within a gaseous or liquid sample. The method includes the steps of (a) contacting the sample with a blue phase-forming liquid crystal composition comprising a nematic liquid crystal and a chiral dopant, and (b) determining the optical changes in the blue phase-forming liquid crystal composition, if any, that arise due to (i) phase transitions in the blue phase-forming liquid crystal, (ii) changes in the pitch of the blue phase-forming liquid crystal or (iii) changes in dimensions of the lattice or lattices of the blue phase-forming liquid crystal. If any such optical changes are observed, this indicates the presence of the target analyte within the sample.

In some embodiments, the target analyte is a volatile organic compound (VOC).

In some embodiments the sample includes (i) ambient air, (ii) a gas carrier that does not trigger a response on the blue phase-forming liquid crystal (including, but not limited to gases such as nitrogen, argon, or hydrogen), (iii) a liquid mixture, or (iv) an aqueous solution.

In some embodiments, the method is performed at 0-65° C. In some such embodiments, the method is performed at 15-40° C. In some such embodiments, the method is performed at room temperature. In some embodiments, the method is performed in thermostatted device.

In some embodiments, the blue phase-forming liquid crystal composition is not disposed on an alignment layer.

In some embodiments, the step of determining the optical changes in the blue phase-forming liquid crystal composition is performed without using polarized light.

In some embodiments, the step of determining the optical changes in the blue phase-forming liquid crystal composition is performed by observing the cholesteric composition with the naked eye.

In some embodiments, the chiral dopant makes up about 30-50% by weight of the cholesteric composition.

In some embodiments, the concentration of the target analyte in the sample is less than 500 ppm. In some such embodiments, the concentration of the target analyte in the sample is less than 200 ppm.

In some embodiments, the chiral dopant is S-811 ((S)-Octan-2-yl 4-((4-(hexyloxy)benzoyl)oxy)benzoate), R-811 ((R)-Octan-2-yl 4-((4-(hexyloxy)benzoyl)oxy)benzoate),

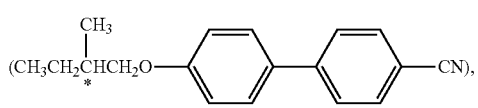

CB 15 ((S)-4-(2-methylbutyl)-4-cyanobiphenyl), S-1011, R-1011, S-2011, or R-2011, or combinations of these compounds. Combinations of chiral dopants can be used to optimize the sensitivity of the blue phase-forming liquid crystal composition to the target analyte.

In some embodiments, the blue phase-forming liquid crystal composition further comprises a non-volatile organic compound that increases the sensitivity of response of the blue phase-forming liquid crystal composition. In some such embodiments, the non-volatile organic compound is a polymer or a polycyclic aromatic compound. In other such embodiments, the non-volatile organic compound is pyrene, phenanthrene, polystyrene, benzoic acid, biphenyl, a halogenated biphenyl, or benzopyrene.

In some embodiments, blue phases of multiple compositions may be used, and analysis of the response of different blue phase compositions can be used to indicate the presence of VOCs. In some cases, each microwell of the array contains a distinct blue phase composition.

In other embodiments, the blue phases are thermostatted at a constant temperature when exposed to the VOCs. In some cases, the temperature at which the blue phases are thermostatted is greater than the ambient temperature. In this case, the process of thermostatting of the blue phase will involve the heating of the blue phase mixture to a desired temperature.

In some embodiments, the target analyte is a VOC comprising an aromatic moiety. In some such embodiments, the VOC is toluene, styrene, xylene, benzonitrile, benzene, or ethylbenzene.

In a second aspect, the disclosure encompasses a device for detecting a target analyte within a gaseous or liquid sample. The device includes a blue phase-forming liquid crystal film that undergoes an irreversible change upon exposure to the sample containing the target analyte.

In some embodiments, the blue phase-forming liquid crystal film comprises a nematic liquid crystal and a chiral dopant.

In some embodiments, at least a portion of the blue phase-forming liquid crystal film has transitioned into a liquid crystal blue phase.

In some embodiments, the sample includes (i) ambient air, (ii) a gas carrier that does not trigger a response on the blue phase-forming liquid crystal film (including, but not limited to gases such as nitrogen, argon, or hydrogen), (iii) a liquid mixture, or (iv) an aqueous solution.

In some embodiments, the chiral dopant makes up about 30-50% by weight of the blue phase-forming liquid crystal film.

In some embodiments, the chiral dopant is S-811 ((S)-Octan-2-yl 4-((4-(hexyloxy)benzoyl)oxy)benzoate), R811 ((R)-Octan-2-yl 4-((4-(hexyloxy)benzoyl)oxy)benzoate),

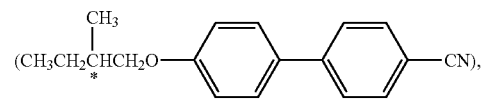

CB 15 ((S)-4-(2-methylbutyl)-4-cyanobiphenyl), S-1011, R-1011, S-2011, or R-2011.

In some embodiments, the blue phase-forming liquid crystal film further comprises a non-volatile organic compound that increases the sensitivity of the response of the blue phase-forming liquid crystal film towards the target analyte. In some such embodiments, the non-volatile organic compound is a polymer or a polycyclic aromatic compound. In other such embodiments, the non-volatile organic compound is pyrene, phenanthrene, polystyrene, benzoic acid, biphenyl, a halogenated biphenyl, or benzopyrene.

In a third aspect, the disclosure encompasses a blue phase-forming liquid crystal composition for detecting a target analyte in a sample. The composition includes a nematic liquid crystal, a chiral dopant, and a non-volatile organic compound that increases the sensitivity of response of the blue phase-forming liquid crystal composition towards the target analyte.

In some embodiments, the chiral dopant makes up about 30-50% by weight of the composition.

In some embodiments, the chiral dopant is S-811 ((S)-Octan-2-yl 4-((4-(hexyloxy)benzoyl)oxy)benzoate), R-811 ((R)-Octan-2-yl 4-((4-(hexyloxy)benzoyl)oxy)benzoate),

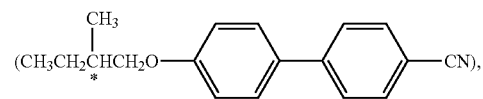

CB 15 ((S)-4-(2-methylbutyl)-4-cyanobiphenyl), S-1011, R-1011, S-2011, or R-2011.

In some embodiments, the non-volatile organic compound is a polymer or a polycyclic aromatic compound. In some embodiments, the non-volatile organic compound is pyrene, phenanthrene, polystyrene, benzoic acid, biphenyl, a halogenated biphenyl, or benzopyrene.

In a fourth aspect, the disclosure encompasses an array device for detecting and/or quantifying a target analyte in a sample. The device contains a plurality of blue phase-forming liquid crystal compositions, each comprising one or more nematic liquid crystals and one or more chiral dopant(s). One or more of the blue phase-forming liquid crystal compositions may also include one or more nonvolatile organic compound(s) that increase the sensitivity of response of the blue-phase-forming liquid crystal composition towards the target analyte. The different compositions may each respond to different concentration levels of the target analyte.

In this disclosure, we also present methods and compositions for producing arrays of isolated LC films with uniform dimensions that are stabilized by capillary forces against gravity, mechanical shock, temperature changes or exposure to solvents. One advantage of this method of preparing LC films is that it may use spin-coating, a widely employed and simple technique to create arrays of LC films with dimensions determined by those of the microwells. Thus, we are able to achieve precise control of the thickness of the LC films. The approach presented here also permits the control the LC anchoring conditions at the substrate, which is difficult to do with other approaches for stabilizing LC films, such as micropillar arrays.

Accordingly, in a fifth aspect, the disclosure encompasses a liquid crystal device having one or more defined surface areas having a liquid crystal thin film disposed thereon, and one or more defined surface areas having no liquid crystal thin film disposed thereon. The device includes (a) one or more first surface areas comprising a liquid crystal-phobic surface, on which no liquid crystal is disposed; and (b) one or more second surface areas that do not comprise a liquid crystal-phobic surface, on which a thin film of liquid crystal is disposed. The one or more first surface areas are raised above the one or more second surface areas by a distance that is equal to or greater than the thickness of the thin film of liquid crystal that is disposed on the one or more second surface areas.

In some embodiments, the liquid crystal-phobic surface includes a superoleophobic surface. In some embodiments, the liquid crystal-phobic surface includes a fluorinated silane or a fluorinated polymer. In some such embodiments, the fluorinated silane is tridecafluoro-1,1,2,2-tetrahydrooctyl)-trichlorosilane.

In some embodiments, the distance by which the one or more first surface areas are raised above the one or more second surface areas, the thickness of the thin film of liquid crystal that is disposed on the one or more second surface areas, or both, are between about 0.1 μm and 100 μm. In some such embodiments, the distance by which the one or more first surface areas is raised above the one or more second surface areas, the thickness of the thin film of liquid crystal that is disposed on the one or more second surface areas, or both, are between about 0.5 μm and 50 μm.

In some embodiments, the one or more second surface areas are the bottom surfaces of one or more microwells embedded in the surface of the device, and the one or more first surface areas are the device surfaces between the embedded microwells.

In some embodiments, the liquid crystal making up the thin film comprises a nematic liquid crystal. In some such embodiments, the liquid crystal making up the thin film further includes a chiral dopant. In some such embodiments, the chiral dopant is S-811 ((S)-Octan-2-yl 4-((4-(hexyloxy)benzoyl)ox y)benzoate), R-811 ((R)-Octan-2-yl 4-((4-(hexyloxy)benzoyl)oxy)benzoate),

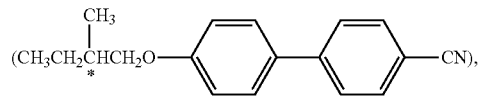

CB 15 ((S)-4-(2-methylbutyl)-4-cyanobiphenyl), S-1011, R-1011, S-2011, or R-2011.

In a sixth aspect, the disclosure encompasses a method of detecting an analyte in a sample. The method includes the steps of contacting a device as described above with the sample, and observing the ordering of the liquid crystal thin film. A change in the ordering of the liquid crystal indicates the presence of the analyte in the sample.

In some embodiments, the ordering of the liquid crystal thin film is observed using polarized light.

In some embodiments, the liquid crystal thin film includes a chiral dopant, and the observed change in the ordering of the liquid crystal is a transition to a liquid crystal blue phase. In some such embodiments, the transition to a liquid crystal blue phase is observed without using polarized light. In other such embodiments, the transition to a liquid crystal blue phase is observed using the naked eye.

In some embodiments, the analyte being detected is a volatile organic compound (VOC).

In a seventh aspect, the disclosure encompasses a method of making the liquid crystal device described above. The method includes the steps of (a) forming a composition having one or more microwells embedded therein, wherein the composition surface between the microwells comprises a liquid crystal-phobic surface, and wherein the bottom surface of the one or more microwells do not comprise a liquid crystal-phobic surface; and (b) filling the one or more microwells with liquid crystal.

In some embodiments, the liquid crystal-phobic surface includes a superoleophobic surface.

In some embodiments, the liquid crystal-phobic surface includes a fluorinated silane or a fluorinated polymer. In some such embodiments, the fluorinated silane is tridecafluoro-1,1,2,2-tetrahydrooctyl)-trichlorosilane.

In some embodiments, the depth of the one or more microwells is between about 0.1 μm and 100 μm. In some such embodiments, the depth of the one or more microwells is between about 0.5 μm and 50 μm.

In some embodiments, the liquid crystal making up the thin film includes a nematic liquid crystal.

In some embodiments, the step of filling the one or more microwells with liquid crystal is performed by spin coating the liquid onto the composition surface.

In some embodiments, the step of filling the one or more microwells with liquid crystal includes the step of applying the liquid crystal to the composition surface and heating the composition surface above the clearing temperature of the liquid crystal. In some such embodiments, the liquid crystal includes a nematic liquid crystal and a chiral dopant.

In some embodiments, the one or more microwells are formed by performing photolithography on the composition, wherein the composition has a liquid crystal-phobic surface, and whereby the liquid crystal-phobic surface is removed from the portion of the composition in which the microwells are formed.

In some embodiments, the one or more microwells are formed by 3-D printing, imprinting, photolithography, additive processes, subtractive processes, stamping or bulk micromachining. In some such embodiments, the liquid crystal-phobic surface between the microwells is formed by chemically activating the surface between the microwells and depositing a liquid crystal-phobic layer onto the chemically activated surface. In some such embodiments, the liquid crystal-phobic layer is deposited by microcontact printing.

Other objects, features and advantages of the present invention will become apparent after review of the specification, claims and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A-3B. (3A) Increasing the weight percent of chiral dopant on the LC led to a decrease on the temperature required for phase transitions. In a parallel experiment, these LC mixtures were exposed to toluene at room temperature and, as shown in (3B), mixtures with a higher concentration of S-811 had higher sensitivity to toluene (24° C.).

DETAILED DESCRIPTION

I. In General

Figures 1A, 1B, 1C, 1D, 1E, 1F:
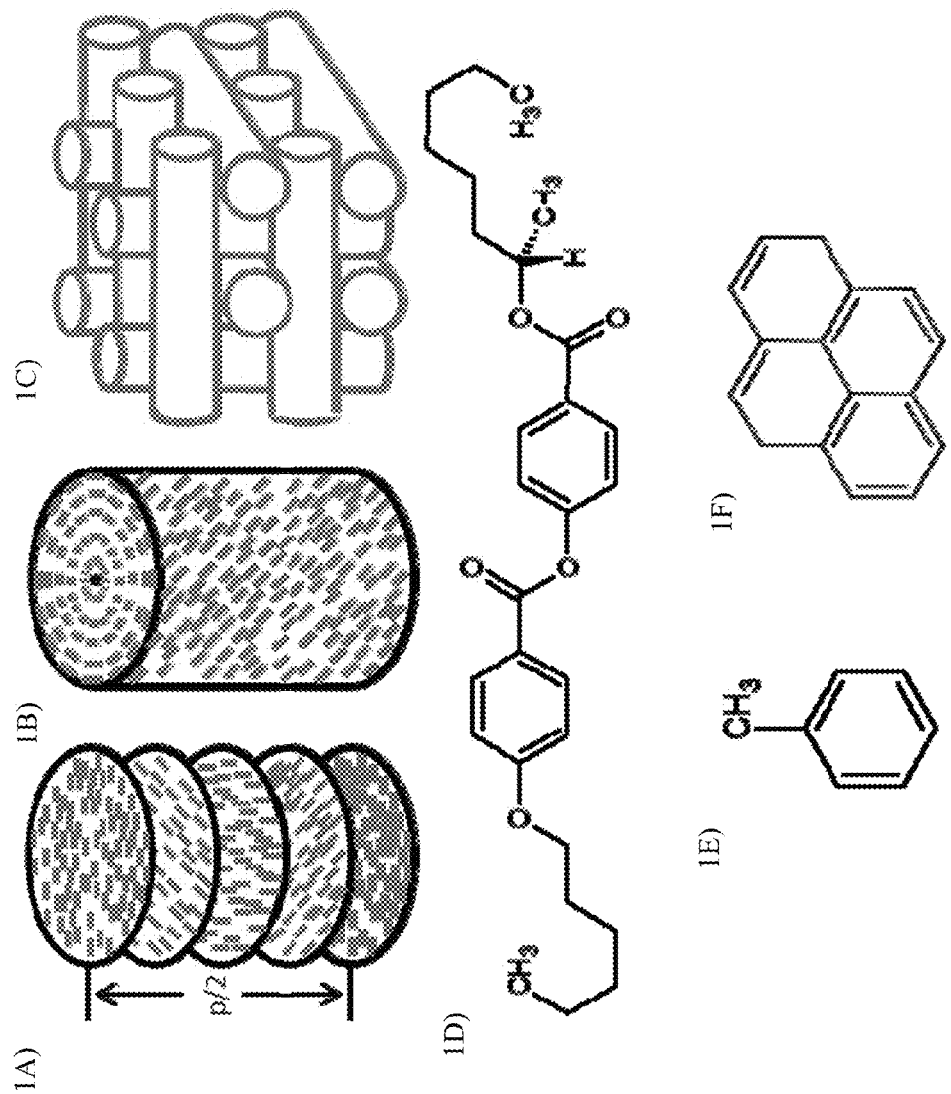
FIGS. 1A-1F. Nematic LCs doped with chiral agents form helical structures in (1A) cholesteric LCs or (1B) blue phases. (1C) The cylindrical structures that characterize blue phases tend to arrange into cubic lattices. In (1D), we present the chemical structure of S-811, the chiral dopant used in this work. The structure of toluene, a volatile organic compound, is shown in (1E). Pyrene (1F) was also used as a non-volatile, non-mesogenic aromatic additive to improve the sensitivity to toluene detection.

The invention is not limited to the particular methodology, protocols, materials, and reagents described, as these may vary. The terminology used herein is for the purpose of describing particular embodiments only, and is not intended to limit the scope of the present invention, which is limited only by the appended claims.

As used herein and in the appended claims, the singular forms "a", "an", and "the" include plural reference unless the context clearly dictates otherwise. The terms "a" (or "an"), "one or more" and "at least one" are used interchangeably. The terms "comprising", "including", and "having" are also used interchangeably.

Unless defined otherwise, all technical and scientific terms used herein have the same meanings as commonly understood by one of ordinary skill in the art to which this invention belongs. All publications and patents specifically mentioned herein are incorporated by reference herein for all purposes, including for describing and disclosing the chemicals, instruments, statistical analysis and methodologies which are reported in the publications which might be used in connection with the invention.

II. The Inventions A. Detecting Volatile Organic Compounds Using Liquid Crystals that Form a Blue Phase Liquid crystals (LCs) are fluids whose constituent molecules have a defined orientational order. The addition of a chiral molecule (i.e., a chiral dopant) to a nematic LC induces a helical distortion in a single direction perpendicular to the director orientation. The resulting chiral mesophases are called chiral nematic or cholesteric (N*) LCs.

At temperatures close to the clearing point, the cholesteric LC can undergo a phase transition into a blue phase (BP), where the helical distortion develops in the two directions perpendicular to the director, forming double twist cylinders form which in turn may self-assemble into a cubic lattice. Accommodating the double twist cylinders in the material requires the formation of disclination lines. By lowering the energy required for the creation of disclination lines, a ternary compound added to the cholesteric LC, such as a volatile organic compound (VOC), permits the helical structures in the N* to relax at room temperature into double twist cylinders of the blue phase and relieve the elastic constraints. This mechanism of target analyte detection can be tuned for maximum sensitivity by varying the proportion of chiral dopant(s) used, and/or by adding a non-volatile organic compound that increases in the sensitivity of response of the blue phase-forming liquid crystal to the target analyte.

Chiral Dopants.

A variety of chiral dopants are known, and the disclosed methods and compositions are not limited to the use of specific chiral dopants. Non-limiting examples of chiral dopants could be added to the nematic LC to produce cholesteric compositions that form blue phases include, without limitation, C15, CB15, S-811, R-811, S-1011, R-1011, S-2011, and R-2011. These dopants are available commercially through EMD Chemicals.

Percentage of Chiral Dopant in the Cholesteric Composition.

The weight % of chiral dopant in the cholesteric composition can be tuned to the desired sensitivity, specific analyte to be detected, temperature of use, and other factors. In certain embodiments, the weight % of chiral dopant can be about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%. In certain embodiments, the weight % of chiral dopant can be within a range defined by any two of these values.

Non-Volatile Organic Compounds.

Non-volatile organic compounds that can be used include the class of all non-volatile organic molecules that are soluble in the BP-forming liquid crystal (i.e., the cholesteric composition) and that lower the temperature and/or target analyte concentration at which the BP-forming liquid crystal responds to the target analyte. Such agents may include, without limitation, polycyclic aromatic compounds, such as pyrene and phenanthrene, polymers, such as polystyrene, benzoic acid, biphenyl, halogenated biphenyls, and benzopyrene.

Target Analytes that Could be Detected.

The BP-forming materials respond to a wide range of target analytes, including, without limitation, VOCs such as toluene, styrene, o-xylene, 1-butanol, ethanol, acetonitrile, dichloromethane, isooctane, and gasoline. Other exemplary VOCs that could be detected include, without limitation, common solvents, such as cyclohexane, diethyl ether, turpentine, acetone, ethyl acetate, hexanes, dioxane, chloroform, tetrahydrofuran, ethyl acetate, isopropanol, n-propanol, dimethylformamide, gasoline, diesel, kerosene, jet fuel, and methyl ethyl ketone. Notably, the sensitivity of the BP-forming materials is highest for VOCs containing aromatic moieties, such as, without limitation, toluene, styrene, xylene, benzonitrile, benzene, and ethylbenzene.

B. Device for Stabilizing and Controlling the Thickness of Liquid Crystal Films

We also disclose herein methods and compositions for producing arrays of isolated LC films with uniform dimensions that are stabilized by capillary forces against gravity, mechanical shock, temperature changes or exposure to solvents. Specifically, liquid crystal-phobic surfaces are used to isolate the domains of liquid crystal films in the microwells of microwell arrays. The liquid crystal-phobic surfaces are located in the spaces between the microwells, while the microwells themselves do not have liquid crystal-phobic surfaces. High throughput methods for LC film deposition, such as spin coating, can be used to create the LC film arrays, because the liquid crystal-phobic surfaces dewet, and the LC films remain only in the microwells. Furthermore, different substrates may be used in the microwells to control the alignment of the isolated LC films.

Liquid Crystal-Phobic Surfaces.

In Examples 2 and 3, the liquid crystal-phobic surface is a fluorinated silane monolayer (tridecafluoro-1,1,2,2-tetrahydrooctyl)-trichlorosilane). However, many other liquid crystal-phobic surfaces could be used to form the liquid crystal-phobic surface outside of the microwells. As a non-limiting example of an alternative method of creating a fluorinated surface, a polymer surface may be directly fluorinated by being exposed to a gas stream containing fluorine ($F_2$) gas. The hydrogen atoms in the polymer surface are replaced with fluorine, resulting in a fluorocarbon layer at the surface that renders the polymer liquid crystal-phobic. Another non-limiting example is plasma fluorination, where a gas stream containing a fluorinated compound, such as $CF_4$, $C_2F_6$, or $SF_6$, is introduced into a plasma, producing fluorine radicals that displace the hydrogen atoms in the polymer surface, leading to the formation of fluorine-carbon bonds (S. Kirk et al. *Plasma Process. Polym.* 2010, 7, 107-122).

The liquid crystal-phobic surfaces are not limited to fluorinated surfaces. A non-limiting example of non-fluorinated surfaces that could be used are so-called superoleophobic surfaces, which are porous topographic structures that capture gas between the liquid and substrate. A variety of methods are known in the art to produce such surfaces.

LCs that could be Used.

The disclosed methods can be used with a wide variety of liquid crystals. Nematic liquid crystals with low viscosity can be used for filling the microwells via spin-coating of the pure liquid crystal material. Non-limiting examples of these low viscosity nematic liquid crystal materials include 5CB, E7, TL205, MBBA, and MLC-2142. A large listing of suitable liquid crystals is presented in "Handbook of Liquid Crystal Research" by Peter J. Collings and Jay S. Patel, Oxford University Press, 1997, ISBN 0-19-508442-X.

Where the viscosity of the liquid crystal is too high for conventional spin-coating, the microwells can still be filled by heating the array containing the microwells and the liquid crystal material above the clearing point temperature of the liquid crystal. This method can be used, for example, to fill the microwells with blue phase-forming liquid crystals, which consist of a nematic liquid crystal, MLC-2142, mixed with high concentrations of a chiral molecule, such as S-811.

Substrates that could be Used in the Microwells.

The surfaces within the microwells are limited only in that they are not liquid crystal-phobic, and a variety of materials and methods can be used to fabricate the microwells. Microwell structures are routinely fabricated onto soda-lime glass slides; however, a wide variety of different substrates, including, without limitation, polymers (e.g., polystyrene, polyimide, polyvinyl chloride, HD-polyethylene, and nylon), oxides (e.g., silicon dioxide, titanium dioxide, aluminum zinc oxide, indium thin oxide, aluminum oxide), nitrides (e.g., silicon nitride, boron nitride), and semiconductors may be used.

Methods of Constructing the Microwell Arrays.

An example of a method that can be used to fabricate the microwells arrays is photolithography, which is illustrated in Examples 2 and 3 below. However, the devices can be constructed using other methods known in the art. Alternative methods for the fabrication of the microwell arrays with liquid crystal-phobic and non-liquid crystal-phobic domains areas include, without limitation, 3-D printing, imprinting, photolithography, additive processes, subtractive processes, stamping or bulk micromachining to produce topographical domains equivalent to the wells where the liquid crystal will be deposited. When using such methods, the surface of the material outside the microwell area would need to be functionalized to render it liquid crystal-phobic. This step can be carried by, for example, chemically activating the surface, and then using microcontact printing to deposit a fluorinated monolayer.

Analytes that could be Detected Using the Thin Film LC Arrays.

The disclosed liquid crystal thin film arrays can be used to detect a wide variety of analytes. As non-limiting examples, thin films of nematic LCs supported on microwells fabricated upon a glass substrate respond to varying concentrations of toluene, cyclohexane, and ethanol. Other solvents would also induce a response in the thin films of nematic LCs, including, without limitation, styrene, o-xylene, I-butanol, ethanol, acetonitrile, dichloromethane, isooctane, and gasoline. In addition, films of blue-phase-forming liquid crystals supported on the microwells respond to a diverse range of analytes.

Alternatively, the microwells can be chemically functionalized after fabrication by exposure to oxygen plasma and subsequent deposition of a metal-containing salt. The metal cation exposed at the interface with the salt is able to form coordinating interactions with nitrile-containing liquid crystals and participate in competitive bonding interactions with molecules containing organophosphonate groups. This mechanism can be used to detect dimethyl methylphosphonate (DMMP) using the disclosed thin film arrays. The microwells also could support LC films that, via competitive coordination interactions with different metal cations, respond to other compounds, including, without limitation, $H_2S$, $NH_3$, 2-chloroethyl ethyl sulfide, and chlorine.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1: Detecting Volatile Organic Compounds Using Liquid Crystals that Form a Blue Phase In this example, we demonstrate the use of blue phase liquid crystals for sensing volatile organic compounds. The use of LC for the detection of VOCs has been reported previously using nematic[6] or cholesteric LC materials,[7] where the analyte induces changes to the bulk properties of the material (like the pitch of the cholesteric helical structures) that leads to a visually detectable signal. However, to our knowledge, blue phase LC materials have not been investigated in the context of chemical sensing applications. Moreover, our approach takes advantage of the elastic properties of the materials to detect VOCs, not changes on pitch as reported previously for cholesteric LCs. The disclosed method of detection based on BP is superior to other methods of VOC detection using LCs because, (i) The LC material does not require an alignment layer, (ii) the method can be performed without the use of light polarizers; (iii) the optical transition in the material induced by the presence of VOCs can be observed with the naked eye; (iv) the sensitivity towards the target analyte can be easily modified via the concentration of a chiral molecules or (v) through the addition of a non-volatile, non-mesogenic aromatic compound; and (vi) the material can be easily processed in such a way that it retains a history of transient exposure to the target analyte.

Background:

Liquid crystals (LCs) are fluids whose constituent molecules have a defined orientational order. As a consequence, these fluids exhibit optical birefringence and respond elastically to deformations of the director, properties that are commonly associated with crystalline solids.[8] The addition of a chiral molecule to the nematic LC induces a helical distortion in a single direction perpendicular to the director orientation (see FIG. 1a). These chiral mesophases are called chiral nematic or cholesteric (N*) LCs.[8]

At temperatures close to the clearing point, the cholesteric may undergo a phase transition into a blue phase (BP) where the helical distortion develops in the two directions perpendicular to the director. Hence, double twist cylinders form which in turn may self-assemble into a cubic lattice (FIG. 1b-c). Three different blue phases exist, in order of increasing temperature, BP I, BP II and BP III. BP I forms a body centered cubic lattice while BP II forms simple cubic lattices.[9] The structure of BP III is not well understood. The double twist structures are locally favored over the cholesteric due to considerations of the elastic energy.[10] However, accommodating the double twist cylinders in the material requires the formation of disclination lines, which are regions of isotropic material.[8-11] By lowering the energy required for the creation of disclination lines, a ternary compound added to the cholesteric, such as toluene, permits the helical structures in the N* to relax into double twist cylinders of the blue phase and relieve the elastic constraints at room temperature.

Procedure:

Solutions in chloroform of MLC-2142 nematic LC and S-811 chiral dopant were prepared and mixed to create mixtures of S-811 in MLC-2142 with concentration from 32.5 wt. % to 50 wt. %. The solvent was then allowed to evaporate for at least 2 days while being sonicated. Films of LC were prepared by depositing the material into microfabricated arrays of microwells and exposed to VOCs using a vacuum system. The details for the fabrication of the wells and the solvent delivery system are known in the art.

Figures 2A, 2B, 2C, 2D:
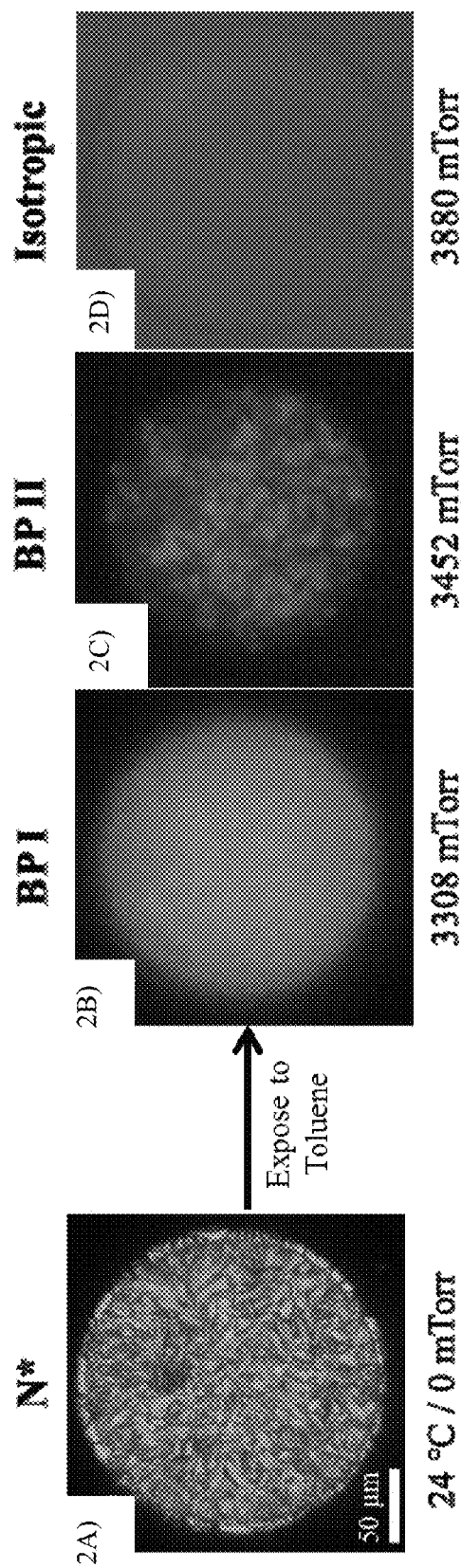
FIGS. 2A-2D. (2A) Sample with 32.5 wt. % of chiral dopant at room temperature. (2B-2C) BP I and BP II are observed by exposing the sample to toluene at 3308 mTorr and 3452 mTorr, respectively. (2D) At 3880 mTorr of toluene, the sample became isotropic. The LC films are 200 µm in diameter and 22 µm thick. Images taken by reflection mode polarized microscopy.

Results:

In our first set of experiments, we characterized the phase behavior of the LC material when exposed at room temperature (~24° C.) to toluene, a model for aromatic VOCs. As shown in FIG. 2, the cholesteric LC undergoes dramatic optical changes when exposed to toluene. For the sample shown in this figure, we used a mixture with 32.5 wt. % of the chiral dopant, which exhibits a transition into the BP I at 3310 mTorr of toluene and a transition into BP II at 3450 mTorr. At 3880 mTorr, the sample became an isotropic liquid. Increasing the concentration of chiral dopant on the N* leads to a decrease in the pitch of the helical structures of the material, which increases the elastic stress stored in the material. The pressure of toluene required for the phase transition of the sample was very sensitive to the weight fraction of chiral dopant. Going from 32.5 wt. % to 45.0 wt. %, the sensitivity of the N*-to-BP I transition to toluene increased almost five-fold from ~3310 mTorr to 720 mTorr. See FIG. 3.

Mechanism:

The experimental results presented in this example suggest the tendency of the cholesteric material to form BPs upon exposure to toluene is a consequence of stabilizing of the disclination cores in the blue phase, which is consistent with the literature on polymer- and particle-stabilized BPs.[12-14] The proposed mechanism for solvent-induced stabilization of the disclination cores in the BP is based on the idea that the isotropic solvent lowers the energy required for the creation of the isotropic material found in the disclination cores. Once the energy barrier for the formation of disclination lines is low enough, the release in elastic energy associated with the double twist structures would lead to the formation of the BP. This hypothesis points to the cholesteric LC as an elastically constrained phase which relaxes into the double twist cylinder upon removal of the energy barrier associated with the creation of isotropic material.

High Sensitivity LC:

With an understanding of the mechanism for solvent-driven cholesteric-to-BP transition, we proceeded to engineer the cholesteric material in order to improve the sensitivity to toluene. Pyrene was added to the BP-forming LC to improve the sensitivity to toluene, because it is a non-volatile, non-mesogenic aromatic compound that serves to further decrease the elastic penalty associated with the creation of disclination lines and, because of its aromatic character. As will be shown below, π-stacking interactions between the aromatic groups of the LC, the pyrene and the toluene enhances the sensitivity of the LC towards toluene.

Figures 4A, 4B, 4C, 4D:
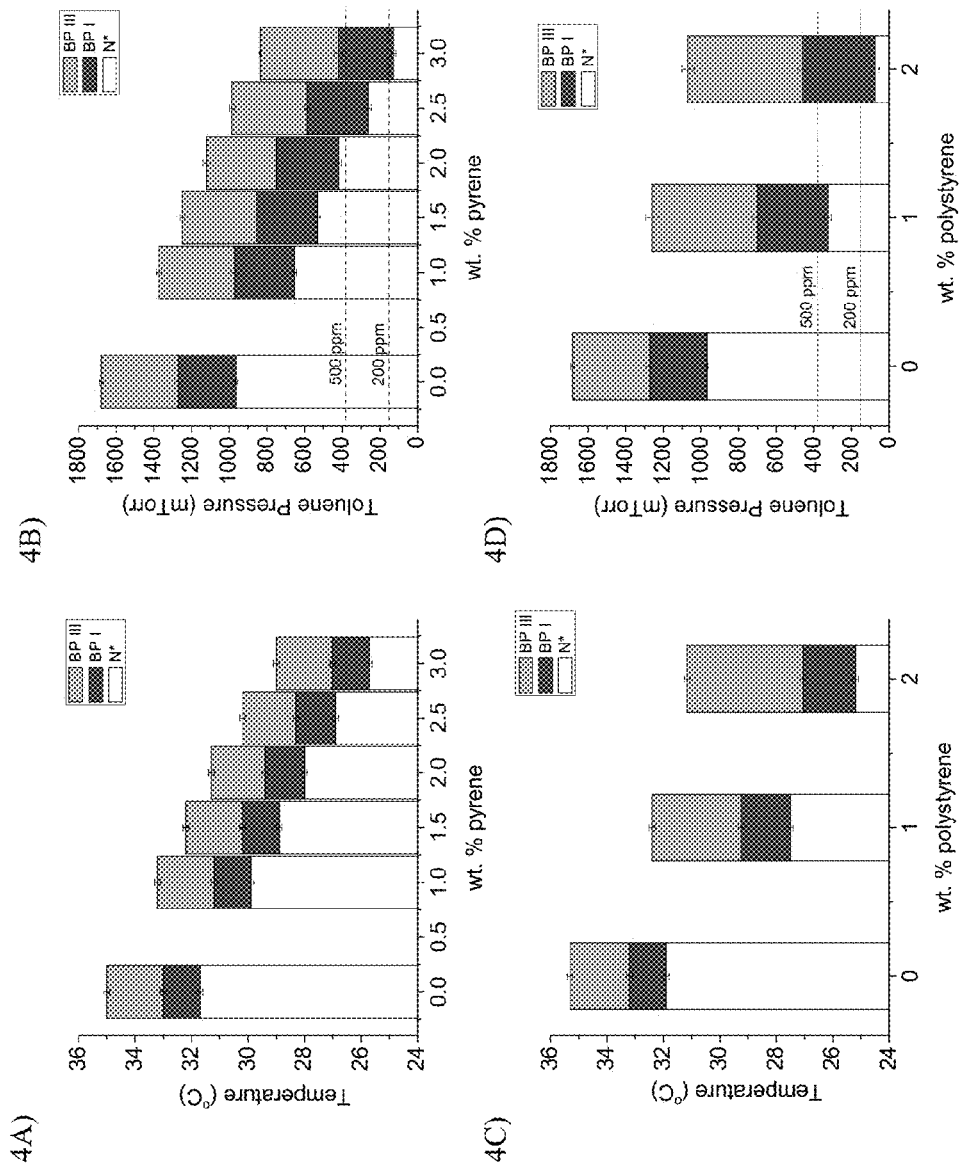
FIGS. 4A-4D. (4A) Addition of pyrene to the BP-forming cholesteric LC (43.5 wt % chiral dopant) led to a decrease in the cholesteric-BP I transition temperature. (4B) The sensitivity to toluene also increases monotonically with pyrene concentration. (4C) Polystyrene leads to a widening of the temperature range of the BP, which is mirrored in a widening of the BP pressure range (4D). For (4B) and (4D), solvent exposure was carried at room temperature (24° C.).

Using a cholesteric with 43.5 wt % of the chiral dopant mixed with different concentrations of pyrene, we observed a monotonic decrease in the cholesteric-BP I transition temperature, and a decrease in the toluene pressure required to trigger this transition (FIG. 4 top). For clarity, the BP I-BPIII and BP III-isotropic transitions are omitted in FIG. 4. These phase transitions into the BP III and the isotropic phase also shift monotonically to lower temperatures/toluene pressures with increasing concentrations of pyrene (FIG. 4a-b). For a mixture with 2.5 wt % pyrene, the sensitivity to toluene was 280 mTorr (FIG. 4 bottom). At atmospheric conditions (760 Torr), the equivalent concentration of 280 mTorr of toluene is 370 ppm, which is well below the 500 ppm 10-minute exposure limit for humans set by the U. S. Occupational Safety and Health Administration (OSHA). For a sample with 3.0 wt % of toluene, the sample responded at 130 mTorr or 170 ppm of toluene, which is below the more stringent limit (200 ppm) for exposure over a period of 8 hours. Similarly, the addition of polystyrene to the BP-forming cholesteric LC with 43.5 wt % of the chiral dopant also led to a decrease in the temperature/toluene pressures at which the phase transitions occurred. (FIG. 4c-d)

Figures 5A, 5B, 5C, 5D, 5E:
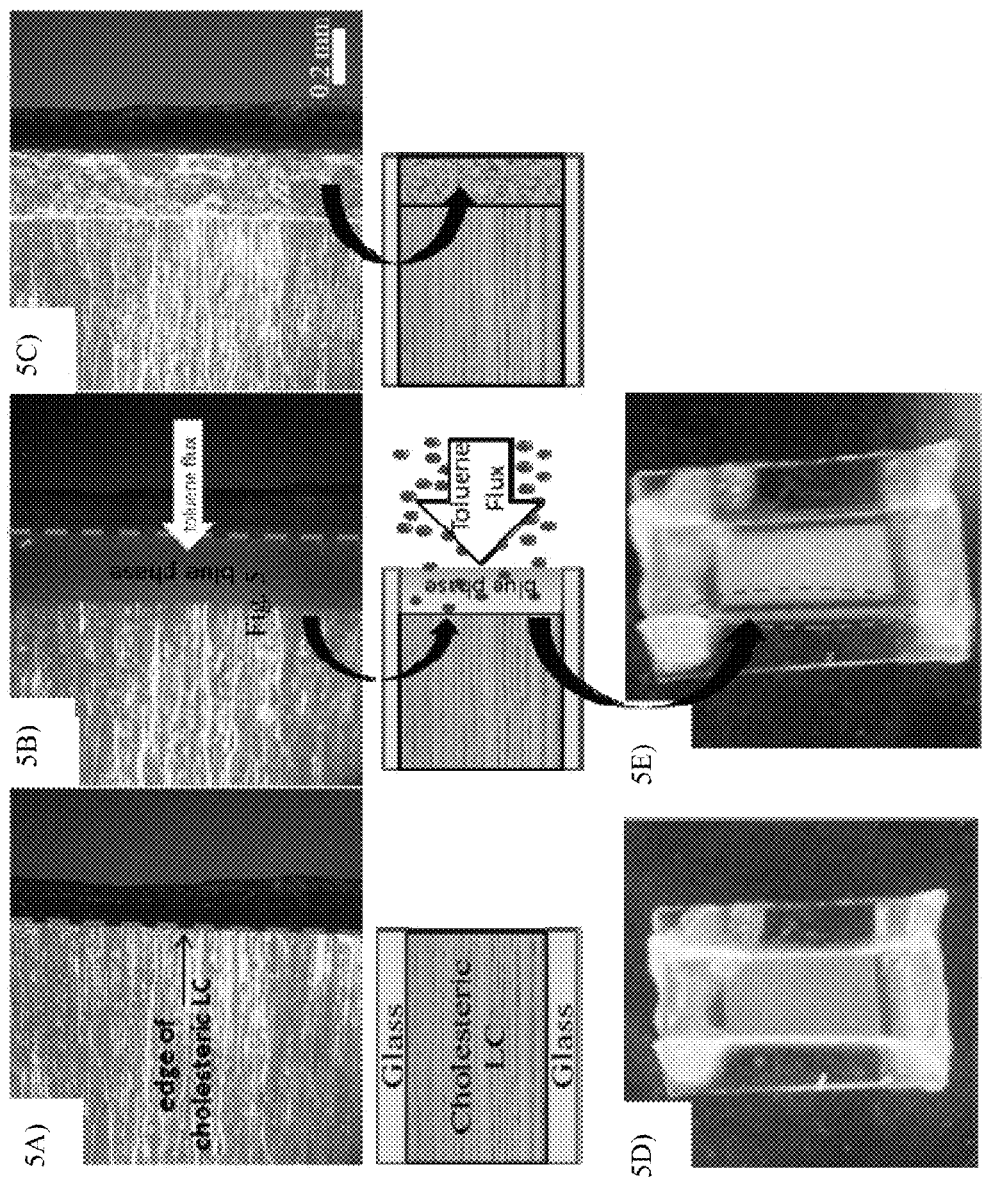
FIGS. 5A-5E. Example of dosimeter based on the cholesteric to blue phase transition of a liquid crystal film. Images correspond to sample before exposure to toluene (5A), during exposure at 1560 mTorr (5B) and two days after initial exposure (5C). Pictures of the dosimeter are shown (5D) before solvent exposure and in (5E) immediately after exposure to toluene.

Dosimeter:

To demonstrate the use of the N*-to-BP transition in practical sensors, a model dosimeter was constructed using two glass chips sandwiched together and separated by 18 µm spacers. The cell was filled with the N*-LC at room temperature under capillary action, which shears the material as it flows into the cell. In this case, we used a mixture with 45 wt % of the chiral dopant (FIGS. 5a and 5d). The cell was then exposed to toluene at 1560 mTorr for 20 minutes.

The toluene diffused into the sides and induced a phase transition into the blue phase. The blue phase front advanced with time of exposure and could be observed with the naked eye, as shown in FIGS. 5b and 5e. After removing the toluene, the material went back into the N* phase. However, the phase transition into the BP allowed the relaxation of the sheared structure of the chiral nematic, so even several days after the exposure a characteristic mark of the front exposed to toluene remains (FIG. 5c). Thus, a permanent record of toluene exposure can be maintained, which can be used for long-term monitoring of exposure to toluene.

Response to Other VOCs:

The goal of our final set of experiments was to investigate the sensitivity of the N* materials to other types of VOCs. Films of N*-LC with 45 wt % of the chiral dopant were exposed to other solvents that might occur as VOCs, such as isooctane (gasoline), dichloromethane (paint strippers), ethanol (personal care products), etc. In previous work with LC-based sensors, the presence of water seemed to affect the response to the target analyte.[15] In this case, an N* to BP transition was not observed even as the sample was exposed to a saturated atmosphere of water vapor. The other VOCs studied here also triggered a phase transition in the N* material. However, in most cases the sensitivity towards toluene was almost an order of magnitude higher than to other compounds. See Table 1. We hypothesize that the relative selectivity towards toluene might be due to π-stacking interactions between the aromatic groups of the LC and toluene.[16, 17]

TABLE 1

Pressure required to induce a cholesteric-BP transition in a sample with 45 wt. % of the chiral dopant.

| | Pressure at cholesteric-BP I transition (mTorr) | Relative Sensitivity |
| --- | --- | --- |
| Toluene | 720 | 1 |
| Styrene | 875 | 1.2 |
| o-Xylene | 1375 | 1.9 |
| 1-Butanol | 2835 | 3.9 |
| Ethanol | >11,000* | >15.2 |
| Acetonitrile | 6700 | 9.3 |
| Dichloromethane | 7805 | 10.8 |
| Isooctane | 6240 | 8.7 |
| Water | No Response | NR |

*Pressure gauge only goes up to 11,000 mTorr

Conclusion:

In summary, we demonstrated a novel approach to detect VOCs based on elastically strained liquid crystal materials. The method of detecting VOCs uses blue phase forming liquid crystals that undergo a phase transition in the presence of VOCs. These materials show preferential selectivity to VOCs with aromatic moieties. Using toluene as a model for aromatic VOCs, we show that high sensitivity towards the target analyte can be achieved by engineering the concentration of chiral dopant or another non-volatile, non-mesogenic aromatic compound in the LC. Moreover, these materials exhibit hysteresis, which can be exploited to maintain a record of transient exposure to the VOC. The advantages of VOC detection using blue phase liquid crystals are: (i) The LC material does not require an alignment layer, (ii) or the use of light polarizers; (iii) the optical transition in the material induced by the presence of VOCs can be observed with the naked eye; (iv) the sensitivity towards the target analyte can be easily modified via the concentration of a chiral molecules or (v) through the addition of a non-volatile, non-mesogenic aromatic compound; (vi) the material can be easily processed in such a way that it retains a history of transient exposure to the target analyte.

These BP-forming LC materials could be useful in power-free, wearable devices for personal exposure monitoring to VOCs. In addition, these devices could find use in applications where it is necessary to passively monitor local concentrations of VOCs such as chemical storage sites, occupational settings, environmental remediation, etc.

REFERENCES CITED (BACKGROUND AND EXAMPLE 1)

[1] OSHA InfoSheet: Toluene Safety in the Workplace. U.S. Department of Labor, Occupational Health & Safety Administration (2013) https://www.osha.gov/Publications/OSHA3646.pdf
[2] Right to Know Hazardous Substance Fact Sheet: Benzene. New Jersey Department of Health (2008)
[3] The Report on Carcinogens: Styrene. U.S. Department of Health and Human Services, National Toxicology Program (2011) http://www.niehs.nih.gov/health/materials/styrene_508.pdf
[4] Leung P L, Harrison R M. Evaluation of personal exposure to monoaromatic hydrocarbons. Occupational and environmental medicine. 1998; 55:249-57.
[5] Harrison R M, Thornton C A, Lawrence R G, Mark D, Kinnersley R P, Ayres J G. Personal exposure monitoring of particulate matter, nitrogen dioxide, and carbon monoxide, including susceptible groups. Occupational and environmental medicine. 2002; 59:671-9.
[6] Drapp B, Pauluth D, Krause J, Gauglitz G. The application of the phase transition in nematic liquid crystals for the optical detection of volatile organic compounds. Fresen J Anal Chem. 1999; 364:121-7.
[7] Chang C K, Kuo H L, Tang K T, Chiu S W. Optical detection of organic vapors using cholesteric liquid crystals. Appl Phys Lett. 2011; 99.
[8] de Gennes P G, Prost J. The Physics of Liquid Crystals. editor. 2nd Edition ed: Oxford University Press; 1995.
[9] Meiboom S, Sammon M, Brinkman W. Lattice of disclinations: The structure of the blue phases of cholesteric liquid crystals. Physical Review A. 1983; 27:438-54.
[10] Meiboom S, Anderson P W, Brinkman W F. Theory of the Blue Phase of Cholesteric Liquid Crystals. Physical Review Letters. 1981; 46:1216-9.
[11] Meiboom S, Sammon M. Structure of the Blue Phase of a Cholesteric Liquid Crystal. Physical Review Letters. 1980; 44:882-5.
[12] Kikuchi H, Yokota M, Hisakado Y, Yang H, Kajiyama T. Polymer-stabilized liquid crystal blue phases. Nature materials. 2002; 1:64-8.
[13] Karatairi E, Rožič B, Kutnjak Z, Tzitzios V, Nounesis G, Cordoyiannis G, et al. Nanoparticle-induced widening of the temperature range of liquid-crystalline blue phases. Physical Review E. 2010; 81.
[14] Ravnik M, Alexander G P, Yeomans J M, Zumer S. Three-dimensional colloidal crystals in liquid crystalline blue phases. Proceedings of the National Academy of Sciences of the United States of America. 2011; 108: 5188-92.
[15] Hunter J T, Abbott N L. Adsorbate-induced anchoring transitions of liquid crystals on surfaces presenting metal salts with mixed anions. ACS applied materials & interfaces. 2014; 6:2362-9.
[16] Hunter C A, Sanders J K M. The Nature of Pi-Pi Interactions. Journal of the American Chemical Society. 1990; 112:5525-34.
[17] Tsuzuki S, Honda K, Uchimaru T, Mikami M, Tanabe K. Origin of Attraction and Directionality of the π/π Interaction: Model Chemistry Calculations of Benzene Dimer Interaction. Journal of the American Chemical Society. 2002; 124:104-12.

Example 2: Device for Stabilization and Thickness Control of LC Films

In this example, we present an approach to produce arrays of isolated liquid crystal (LC) films with uniform dimensions that are stabilized by capillary forces against gravity, mechanical shock, temperature changes or exposure to solvents. Arrays of microwells were fabricated through lithographic techniques. The novelty of our method is in the use of fluorinated monolayers to isolate domains that are preferentially wetted by the LC. Thus, high throughput and simple techniques for film deposition, such as spin-coating, can be used to create arrays of individual LC films. In addition, different substrates may be used to control the alignment of LC molecules at the interface.

Procedure:

To control the thickness of the LC films, arrays of microwells were fabricated using conventional lithography techniques for SU-8 photoresist. SU-8 photoresist solutions with different concentration of solids were spin-coated onto glass microscope slides at different spin speeds to obtain films with thickness in the range of 0.7-30 µm. The thickness of the SU-8 films was measured after development of the photoresist using a profilometer. Soft bake, UV exposure and post-exposure bake were carried according to the manufacturer specifications. Before solvent development of the photoresist, the SU-8 surfaces were exposed to an oxygen plasma (250 W RF power, 50 $cm^3$/min oxygen) and subsequently functionalized with (tridecafluoro-1,1,2,2-tetrahydrooctyl)-trichlorosilane.

Development of the photoresist proceeded by sonication of the samples for 2-5 minutes in SU-8 developer. The samples were then rinsed with ethanol and dried under a stream of nitrogen. A final baking step was carried at 110° C. for 7-10 minutes to remove any remaining solvent and to anneal the final structure. See FIGS. 6a-d.

To deposit the LC film, we spincoated a 5 µL droplet of pure LC at room temperature on top of the fabricated structures. In this example, 4-cyano-4'-pentylbiphenyl, 5CB, was used as a representative LC. However, any other type of LC could also be spincoated into the microwell arrays.

Figures 6A, 6B, 6C, 6D, 6E, 6F:
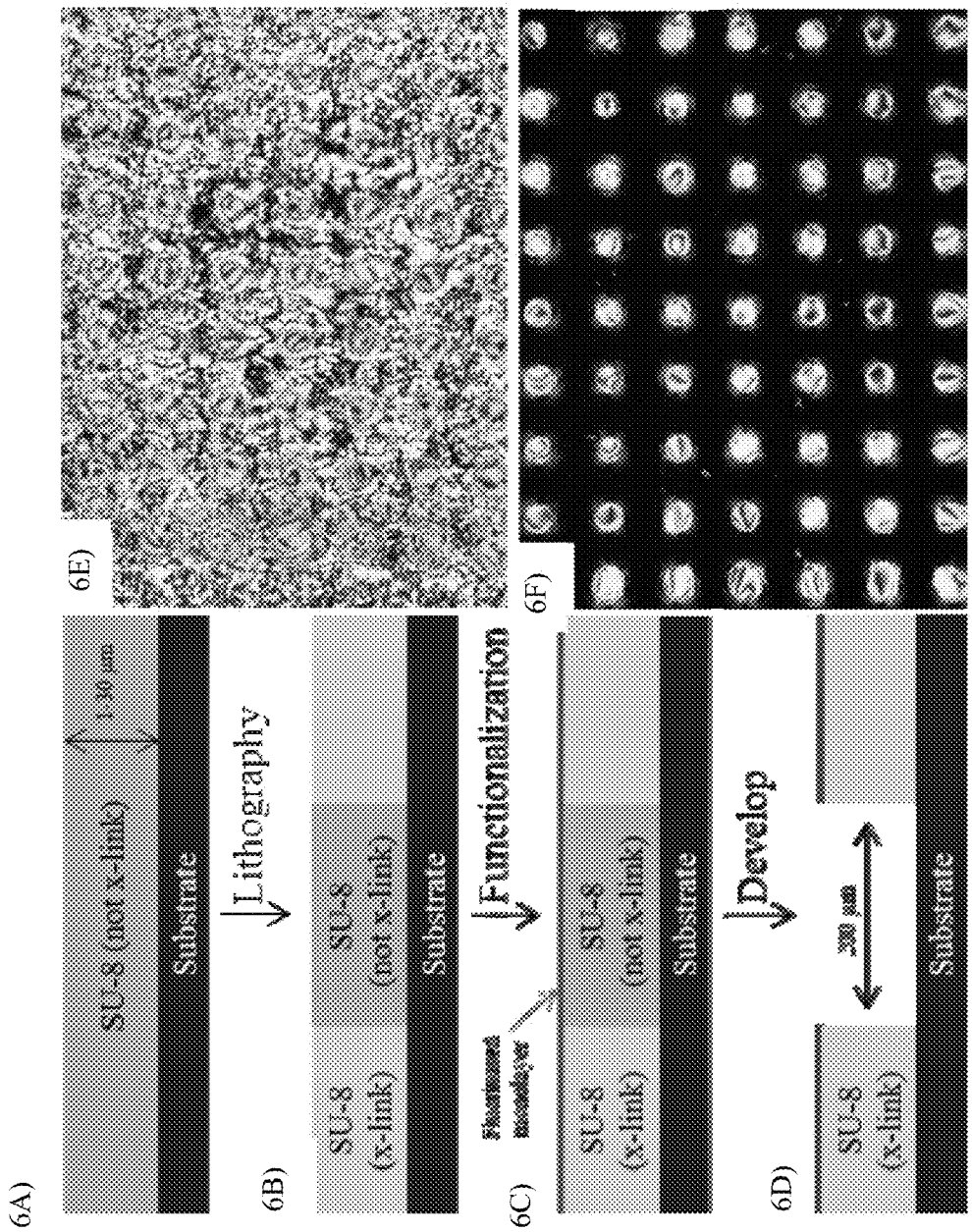
FIGS. 6A-6F. (6A, 6B, 6C and 6D) Schematic of procedure for fabrication of functionalized microwells. Without functionalization with a fluorinated monolayer, spincoating 5CB into the arrays led to the formation of an undesirable interstitial film (6E). Functionalization of the area outside the microwells facilitated the production of an array of isolated LC films (6F). For these samples, the depth of the microwells was 29.9 µm.

Control of LC Film Thickness:

In our initial experiments, we found that it was very difficult to routinely fill these microfabricated wells with LC (FIG. 6e), so we treated the surfaces of the microwells with fluorinated monolayers that promoted dewetting of the LC from the regions between the microwells. This led to precise filling of the microwells and precise control of the thickness of the LC films (FIG. 6f).

Figure 7:
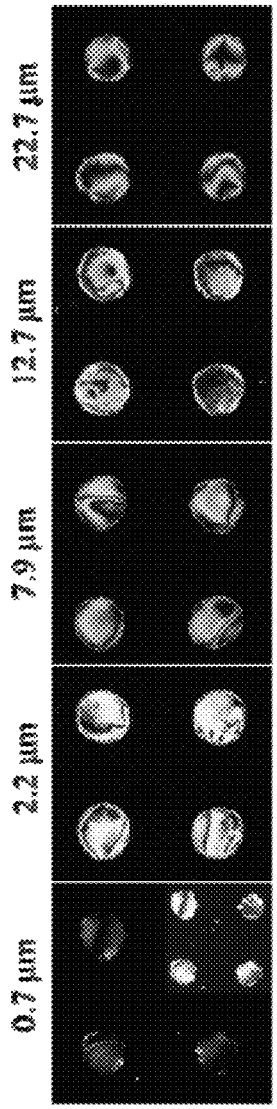
FIG. 7. (Top) Representative images of LC films supported on microwells with different thickness of the SU-8 photoresist and viewed between cross-polarizers. The number atop each image is the thickness of the SU-8 film. For the 0.7 µm wells, the top image corresponds to capture conditions consistent with the other images while the inset image was taken with enhanced image capture settings. The diameter of the microwells was 200 µm. (Bottom) Retardance of LC films compared to the depth of microwells.
Figure 7:
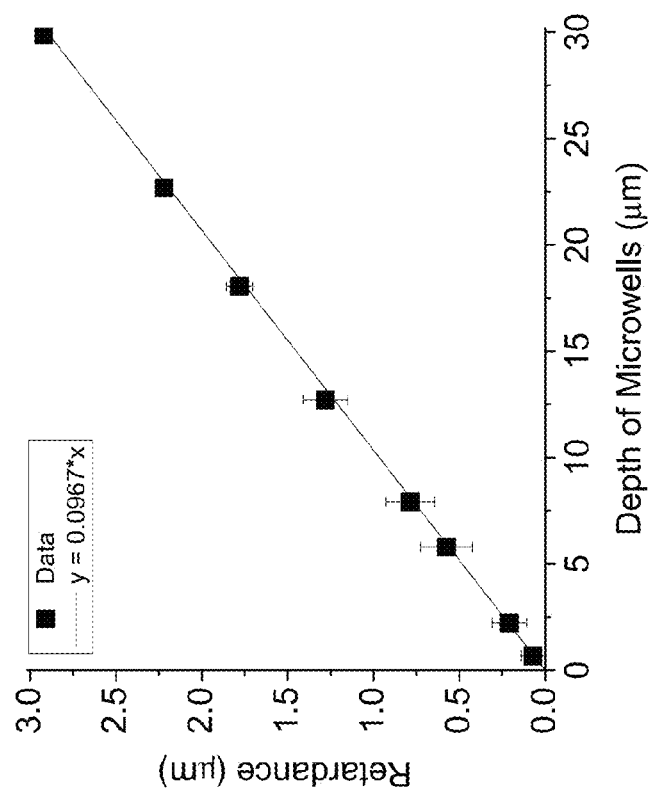
Figure 8:
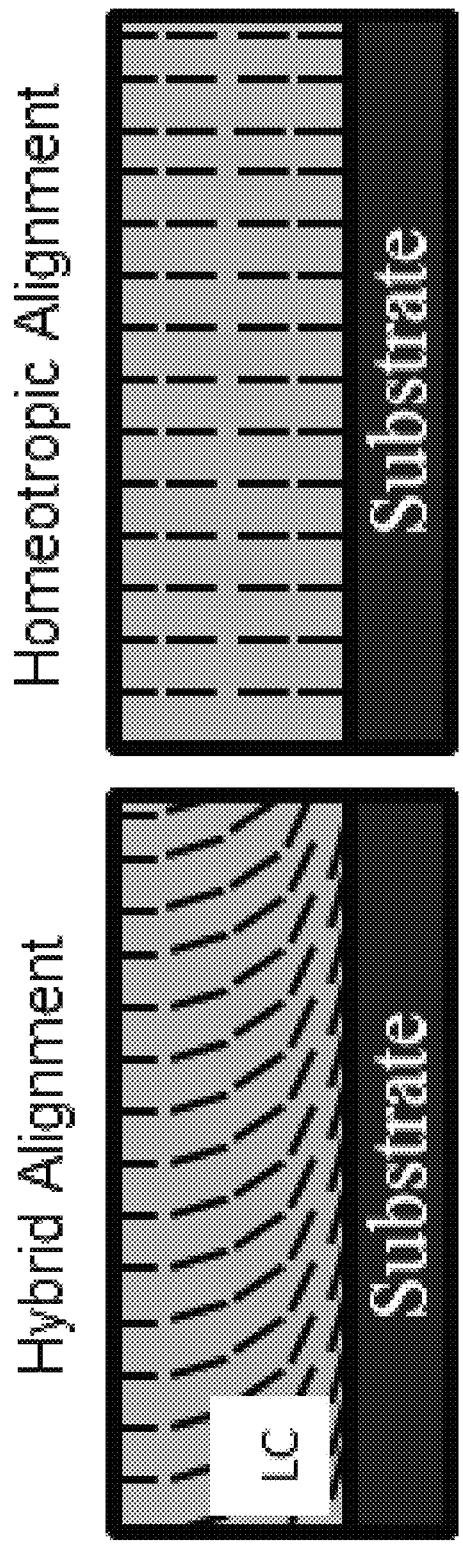
FIG. 8. Different types of substrates promote different alignment conditions of the LC at the substrate-LC interface. In the cartoons, it is assumed that the top interface of the LC is exposed to air, which makes the LC molecules align perpendicular to the surface. The substrate may induce planar (left) or homeotropic (right) alignment. In a nematic LC film subject to hybrid alignment, one of the surfaces induces homeotropic alignment while the other one induces planar alignment. In order to satisfy both boundary conditions, the director orientation changes uniformly along the thickness of the film.

Representative images of the arrays of LC films (0.7-30 µm thick and 200 µm diameter) viewed through cross-polarizers are presented in FIG. 7. At the glass interface, the molecules of the LC orient parallel to the substrate (planar alignment) while at the air interface, the molecules are oriented in the direction perpendicular to the interface (homeotropic alignment). Under these boundary conditions, the LC film is said to be under hybrid alignment (see FIG. 8). When viewed through cross-polarizers, the black areas on the images of FIG. 7 result from the lack of birefringent material while the LC films appear bright and with different colors, depending on their thickness.

To confirm thickness of the LC films, we measured the retardance of polarized light traveling through the birefringent LC films. For 5CB with planar alignment at the glass interface and homeotropic alignment at the free surface, the effective birefringence is 0.0967. The retardance, however, depends linearly on the thickness of the sample. As shown in FIG. 7, we found excellent agreement between the measure retardance of the LC films and the depth of the microwells, which confirmed the control over the thickness of the LC films furnished by the microwell arrays.

Control of LC Anchoring:

The orientation of the LC molecules at the substrate can be easily manipulated using substrates other than glass or by functionalizing the surface of the glass. The different orientations of the LC molecules at the surface can be visualized through polarized microscopy. For example, a LC film subject to hybrid alignment conditions would appear bright and colored, as shown in FIG. 7. However, a LC film deposited on a substrate that induces homeotropic alignment would appear dark when viewed through cross-polarized light. This manipulation of the anchoring conditions of the LC, coupled with the exquisite control of film thickness, could render the microwell arrays of critical importance in applications where control of surface chemistry and thickness control of LC films is necessary.

Figures 9A, 9B, 9C, 9D:
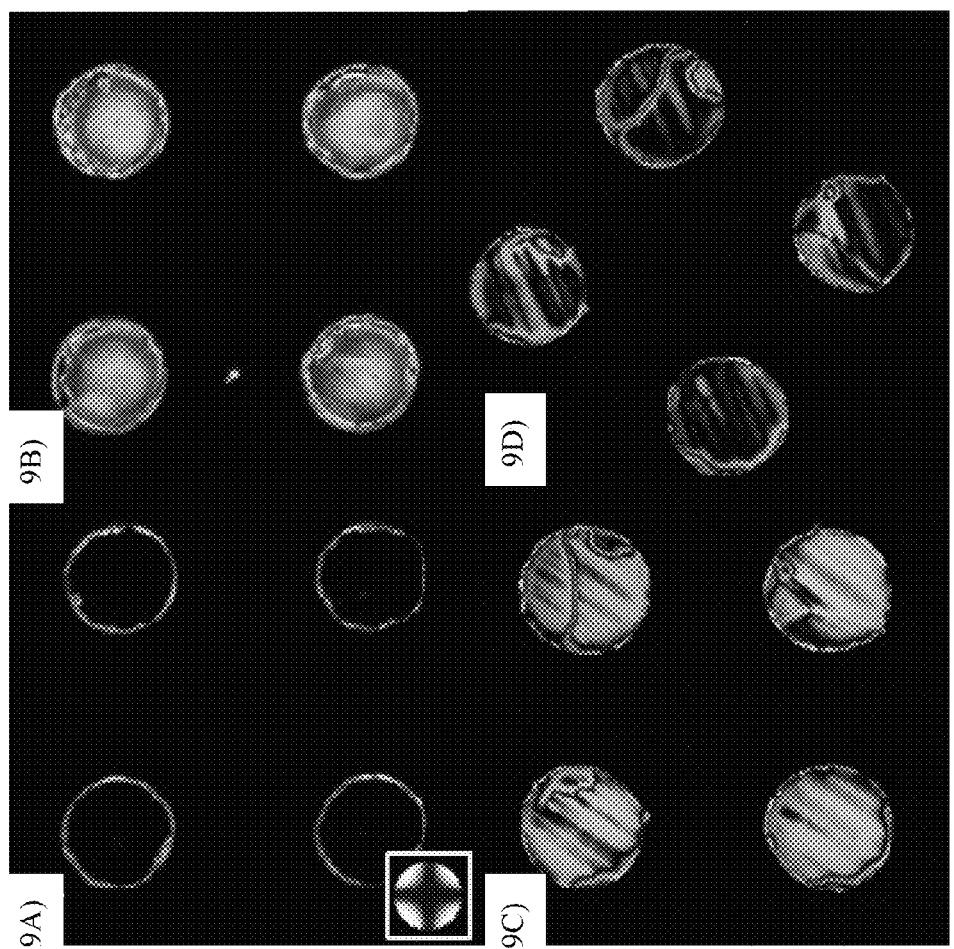
FIGS. 9A-9D. Examples of LC films supported surfaces that induce (9A) homeotropic, (9B) planar and (9C-9D) azimuthal alignment. The surface of the microwells were functionalized with (9A) Al(ClO$_4$)$_3$, (9B) gold and (9C-9D) rubbed polyimide. The diameter of the microwells is 200 µm and the SU-8 film thickness is 7.9 µm for all samples shown in the figure.

To demonstrate the control of surface anchoring on the LC afforded by our approach, we functionalized microwell arrays with different materials such as aluminum perchlorate ($Al(ClO_4)_3$), gold, and polyimide that was subsequently rubbed with a cloth. The LC exhibits homeotropic alignment at the aluminum perchlorate interface (see FIG. 9a). In contrast, gold induces planar alignment of the LC molecules (FIG. 9b). Polyimide also induces planar alignment in the LC. However, rubbing the polyimide with a cloth produces microscopic ridges that tend to orient the LC molecules at the substrate in a preferential azimuthal direction. This preferential alignment is observed by rotating LC sample with respect to the orientation of the cross-polarizers. In FIG. 9c, an LC sample on a rubbed polyimide film appears bright because it is not aligned with the polarizers. In contrast, when the sample is rotated such that the alignment direction of the LC is parallel to the direction of one of the polarizers (FIG. 9d) the sample appears dark. This control of the azimuthal direction of the LC at the substrate would be impossible to reproduce using other techniques for stabilizing LC films, such as micropillar arrays.

Conclusion:

In summary, we present a method for stabilizing LC films with thickness in the micrometer range. Our method uses spin-coating, a widely used and simple technique to create arrays of LC films with dimensions determined by those of the microwells. Moreover, our approach allows for careful control of the surface anchoring conditions of the LC films inside the microwells. The precise control of dimensions and surface anchoring conditions of the LC films can be used in sensing technologies, next generation LC displays, medical devices, and other LC-based applications.

Example 3: Using LC Thin Films for VOC Sensing Applications

Figure 10:
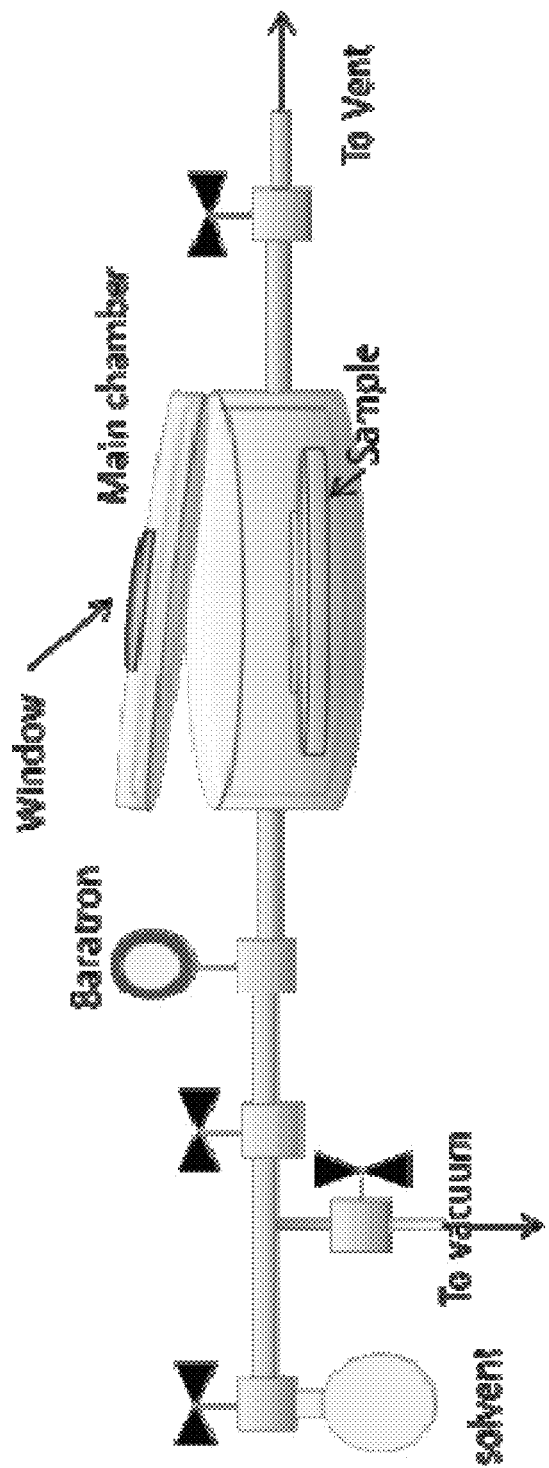
FIG. 10. Schematic of solvent delivery system used to study the optical response of LCs to different gaseous analytes. The exposure system consists of a small chamber connected to a vacuum pump and a series of valves for solvent delivery. The cylindrical chamber has thick glass windows at the top and bottom sides and is mounted on the stage of a polarizing microscope. Before a sample was loaded into the chamber, the solvent was degassed by three cycles of the freeze-pump-thaw technique. During operation, the glass chip containing the 5CB-filled microwell array was placed in the main chamber, the top cap was tightly sealed and the whole system was pulled under vacuum for 10-15 minutes to remove air, water and other organic contaminants that might affect the optical response of 5CB. The minimum pressure obtained in the vacuum chamber was of ~315 mTorr. In comparison, the vapor pressure of 5CB is ~5×10-mTorr at room temperature (~23° C.) so it was not expected that, under the range of pressures reported in our experiments, 5CB had a significant evaporation rate that would lead to mass loss in the film. After evacuation of the system, the solvent was delivered into the main chamber by manually operating the valves that lead from the solvent container to the chamber. Toluene vapor was introduced in a series of step increments of pressure with a time intervals of ~2-4 minutes between each step to allow for equilibration of toluene between the vapor and 5CB. The equilibrium state was observed by stabilization of the solvent pressure and the optical response of the 5CB. The pressure of the system was monitored using a BARATRON® capacitance manometer and manually recorded.

In this example, we demonstrate that LC films formed using the methods of Example 2 can be effectively used to detect toluene, a model VOC. First, we created arrays of microwells to support and stabilize micrometer-thick films of LC with hybrid anchoring conditions. After placing the liquid crystal (LC) films under vacuum, they were exposed to controlled pressures of toluene vapor (see FIG. 10). Introduction of toluene into the system led to dramatic optical changes in the film (FIG. 11), culminating in a film that appeared dark with bright rims (consistent with uniform homeotropic alignment of the LC). This result indicated that toluene induced an alignment transition of the LC film at the interface with the substrate, from planar to homeotropic. This planar-to-homeotropic anchoring transition is the result of weakening of the anchoring energy at the substrate relative to the elastic energy of the LC and the anchoring energy at the free interface.

Procedure:

Films of SU-8 photoresist were deposited into clean glass or polyimide-coated slides and photo-polymerized to the desired pattern (in this case, circles with 200 µm diameter). Before pattern development, the samples where functionalized with a fluorinated monolayer. After development, a droplet of pure 5CB was deposited on top of the samples and spincoated. The depth of the microwells, determined with a surface profilometer, was between 7-30 µm. Some microwells were further functionalized with a gold substrate (see FIG. 9).

Results:

The boundary conditions at the interphases ensure that the LC orientation is parallel at the substrate (glass, gold, P1) and perpendicular at the free interface (vacuum). This hybrid alignment makes the LC films appeared colored when viewed through cross-polarizers. Introduction of toluene into the system led to changes in the director profile and to the 5CB ordering, which were evidenced as dramatic optical changes in the 5CB film (see FIG. 11).

Figures 11A, 11B, 11C, 11D, 11E:
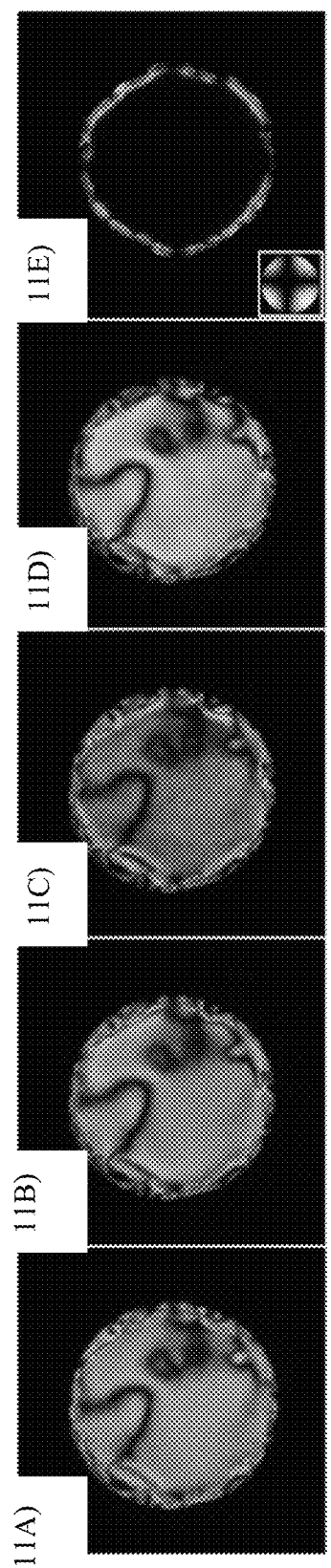
FIGS. 11A-11E. Film of 5CB supported on a microwell and exposed to different pressures of toluene: (11A) 0 mTorr, (11B) 1410 mTorr, (11C) 1450, (11D) 1520 mTorr and (11E) 1570 mTorr. Diameter of microwell was 200 µm and the thickness of the LC film was 14.9 µm. In this case, the surface of the microwell was glass. However, substrates of gold, polyimide and polystyrene have also been used for detection of toluene.
Figures 12A, 12B, 12C, 12D:
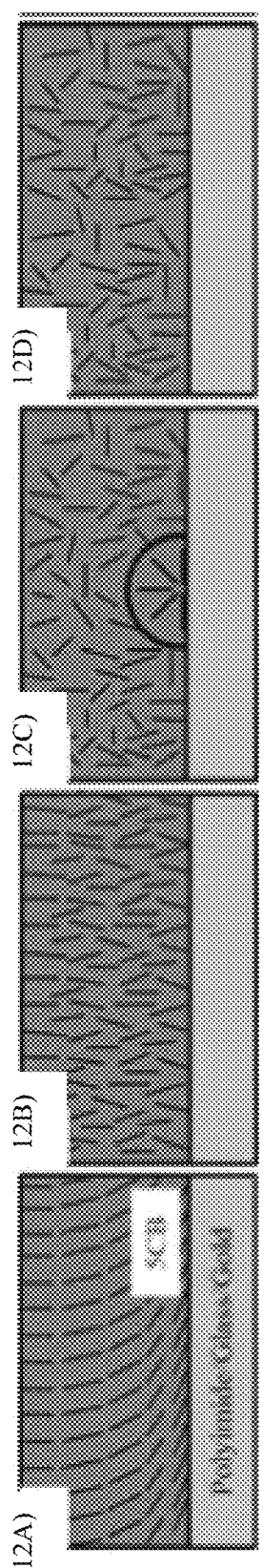
FIGS. 12A-12D are diagrams showing LC alignment as toluene concentration is increased from lower concentrations (12A) through intermediate concentrations (12B, 12C) to higher concentrations (12D).
Figure 13:
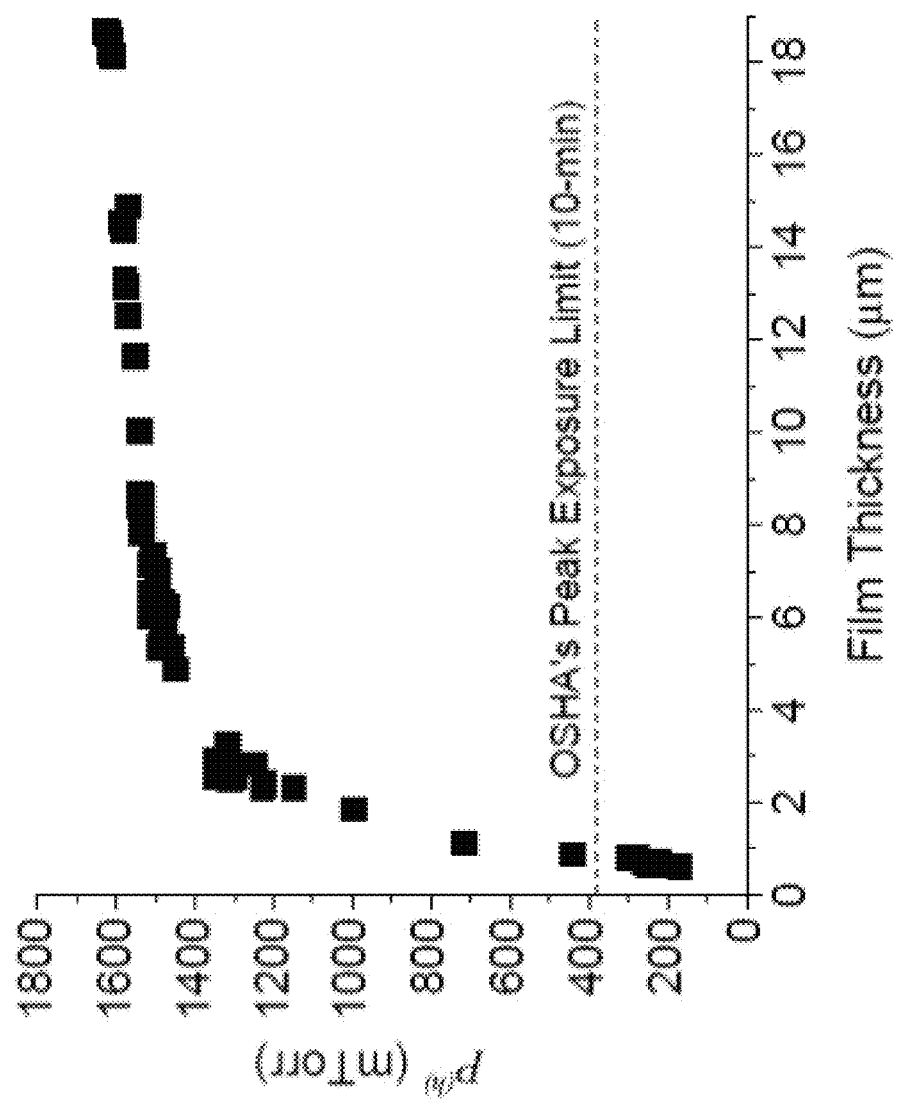
FIG. 13. The effect of LC film thickness on the pressure of toluene required for planar-to-homeotropic transition in 5CB. Black squares represent experimental data.

At a certain pressure of toluene, P(h), the alignment of the LC at the surface became perpendicular (FIG. 12b). This anchoring transition was found to depend on the thickness of the LC film (FIG. 13) and the chemistry of the substrate, indicating an interplay between the surface anchoring and elastic energies in the LC (FIG. 11a).

Conclusion:

This example reveals the existence of an ordering transition (planar-to-homeotropic orientation) within micrometer thick films of 5CB that is induced by toluene, providing a potential method for detecting VOCs. Ongoing studies seek to decrease the pressure of toluene required to bring about the anchoring transition in the LC by lowering the anchoring energy between the LC and supporting substrate.

Example 4: Toluene-Induced Phase Transitions in Blue Phase Liquid Crystals

This example extends and provides more details regarding Example 1, which the demonstrated the use of blue phase liquid crystals for sensing volatile organic compounds. In this example, we report phase transitions in blue phase-forming liquid crystals (LCs) that are triggered by exposure to toluene vapors. Specifically, the phase behaviors of mixtures composed of the mesogens MLC-2142 and chiral dopant S-811 were characterized as a function of temperature and exposure to toluene. These measurements revealed that room-temperature cholesteric phase mixtures MLC-2142 and S-811 could be induced to form blue phases (BPs) with increasing vapor pressure of toluene.

Our results suggest that the absorption of toluene into the BP-forming LCs lowers the energy required for the formation of disclination cores in the BP phase, thus allowing the elastically-favored double twist cylinders to form at lower temperatures. This conclusion is supported by spectroscopic characterization of Bragg reflections associated with the pitch of the BP-forming cholesteric LC, which revealed that toluene has only a modest effect on the pitch. For example, the pitch of the BP-forming cholesteric containing 32.5 wt. % of S-811 decreased by 7 nm after being exposed to 3500 mTorr of toluene. Consistent with our hypothesis, we interpret the main effect of toluene to be to lower the order-disorder transition temperature of the LC.

Similar to toluene, experiments with BP-forming mixtures containing non-volatile molecules (pyrene or RM257) revealed that these compounds have a pronounced effect on the order-disorder transition temperature but do not significantly affect the pitch of the cholesteric LC. Finally, we demonstrate that BP-forming LCs containing pyrene can be used to detect toluene at concentrations below 200 ppm. Overall, these results guide the design of LC-based materials that respond to VOCs such as is needed in occupational settings.

Introduction

Liquid crystals (LCs) are fluids composed of molecules that exhibit long-range orientational order. In LCs, the preferred orientation of the molecules within a local region of the phase is represented by a headless vector called the director. The addition of chiral molecules to a nematic LC typically induces a helical strain in a single direction perpendicular to the local orientation of the director (see FIG. 14A).

In these chiral mesophases (called cholesteric LCs), the distance required for one rotation of the director (the pitch, p) depends on the nature of the chiral dopant and its concentration in the LC.[1] Typically, the relationship between the concentration of a given chiral agent (c) and the pitch (p) of the resulting cholesteric LC is pc=H, where the constant H is the so-called helical twisting power of the chiral agent in the mixture. When cholesteric phases possessing small helical pitches (<500 nm) are heated to a temperature just below the order-disorder transition temperature at which the isotropic phase appears, so-called blue phases (BP) are observed to form.[2] The BPs are characterized by the presence of twist in two directions orthogonal to the director, which results in the formation of double-twist cylinders (FIGS. 14B and 14C).

Three different BPs have been identified, each of which differ by the arrangement of the double-twist cylinders. Specifically, the cylinders self-assemble into periodic cubic lattices in BP I (body-centered cubic) and BP II (simple cubic, see FIGS. 14D-14F.[3,4] The structure of BP III, in contrast, comprises randomly oriented double-twist cylinders.[5] For a particular BP-forming LC, BP I is observed at lower temperatures than BP II or BP III.[2,3]

Figures 14A, 14B, 14C, 14D, 14E, 14F, 14G:
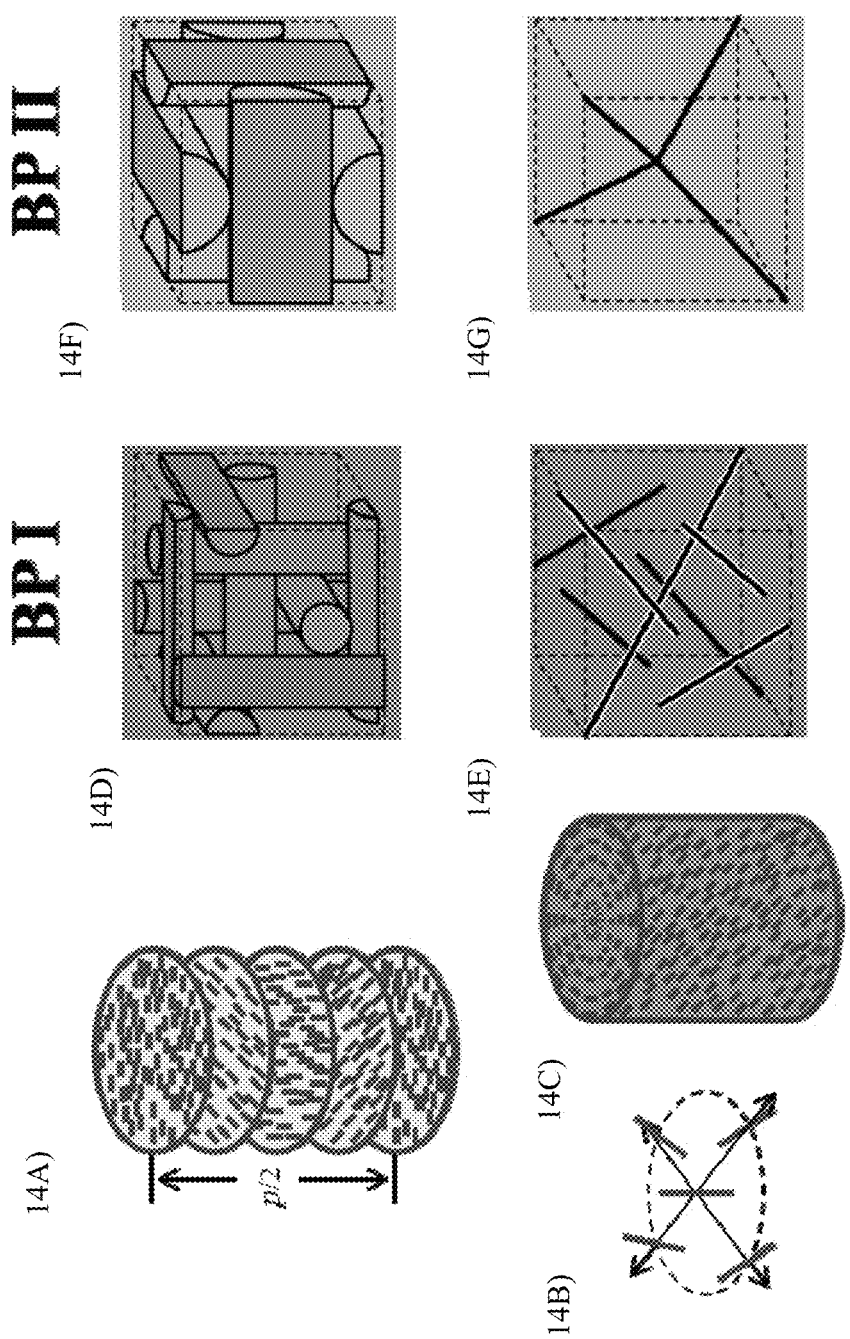
FIGS. 14A-14G. (14A) Cholesteric LCs are characterized by a helical distortion in the direction perpendicular to the director. Bars represent local director orientations. (14B) In BPs, the helical twist develops in two directions perpendicular to the director, forming the cylindrical structures shown in (14C). These cylindrical LC structures self-assemble into cubic lattices: (14D) body-centered cubic for BP I and (14F) simple cubic for BP II. Cylinders represent double-twist cylindrical structures. (14E) Lattice of disclination lines (dark lines) associated with BP I. (14G) Lattice of disclination lines (dark lines) associated with BP II.

We note that formation of the double twist structures that give rise to BPs is locally favored over the cholesteric by elastic energy effects.[1,6] However, accommodating the double twist cylinders requires the formation of (−½) disclination lines, which are regions in which the local order of the mesogens is lower than the bulk (FIGS. 14E and 14F). For this reason, BPs are typically only observed at temperatures close to the clearing point of the LC material. Well below this temperature, the energetic penalty associated with the disordered core of the −½ disclination suppresses the formation of the BPs.

Past studies of BPs, however, have revealed that polymers or nanoparticles can accumulate within the cores of the disclinations lines and increase the temperature range over which the BP is stable.[7-10] The proposed mechanism for stabilization of the BP is the replacement of the energetically costly region of the disclination core by polymers or nanoparticles. In general, the partitioning of the polymer and nanoparticles into the defects is aided by the low miscibility of these species in the bulk cholesteric LC.[11] This conclusion emphasizes the character of the BP as being comprised of coexisting nanoscopic regions that are locally disordered (defect cores) and regions that are ordered and anisotropic (double twist cylinders). Although the above descriptions suggests that other types of additives that influence this nano-phase separation should also affect the temperature range over which the BP is observed, to our knowledge, the role of small-molecule additives on BP stability has not received substantial attention. The work reported in this example aimed to elucidate the effect of small achiral molecules on the phase behavior of BP-forming LCs.

Figure 15:
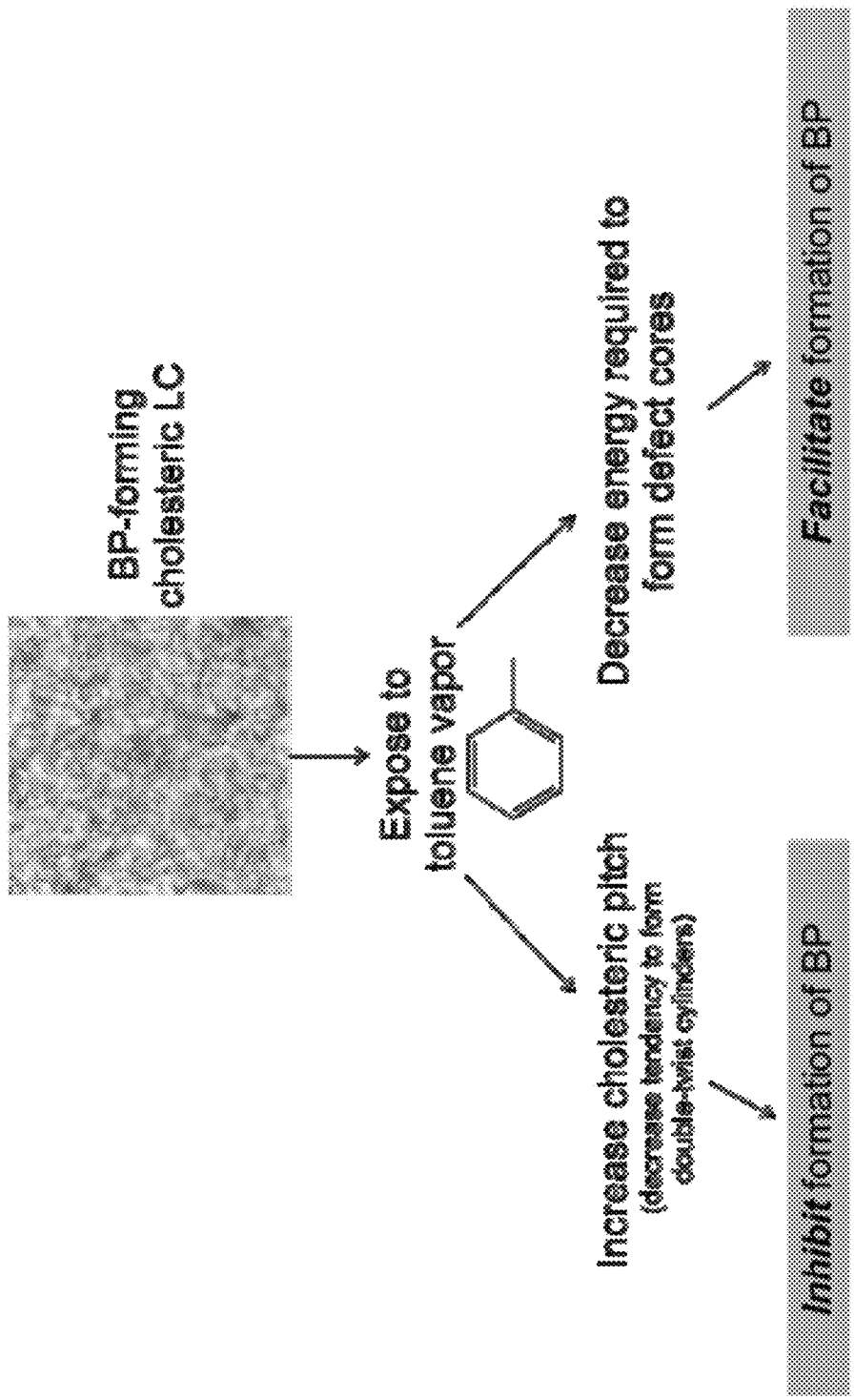
FIG. 15. Room-temperature exposure of BP-forming cholesteric LCs to vapors of small achiral molecules such as toluene can inhibit or facilitate the formation of the BP. In Example 4, we investigate the dominant effect of toluene on the phase behavior of BP-forming LCs.

We hypothesized that small molecules may influence the phase behavior of BP-forming LCs through two possible mechanisms. First, past studies have demonstrated that small organic molecules such as toluene cause an increase in the helical pitch of cholesteric LCs.[12-15] At sufficiently high concentrations of toluene, cholesteric LCs undergo phase transitions into an isotropic phases. Based on this prior observation with cholesteric LCs, we hypothesized that toluene may inhibit the formation of double twist cylinders, thus leading instead to a direct from a cholesteric phase to an isotropic phase. This prediction is based on the observation that formation of BPs require cholesteric pitches of <0.5 μm,[2] whereas the exposure of LC samples to toluene vapors leads to an increase in the cholesteric pitch. Alternatively, we hypothesized that toluene may decrease the energy penalty associated with the formation of disclination cores, allowing the cholesteric to form the double twist cylinders (thus, forming defects) and transition into the BP at low temperatures. In this example, we sought to determine the dominant effect of toluene on the phase behavior of BP-forming LCs (See FIG. 15).

In this example, we report that BP-forming LCs equilibrated against increasing concentrations of vapors of toluene undergo several phase transitions at room temperature (cholesteric-to-BP I, BP I-to-BP II, BP II-to-BP III, etc.). To probe the mechanism underlying this observation, we investigated the phase behavior of mixtures of BP-forming LCs with a range of structurally diverse non-volatile organic compounds. We find that the phase behavior and temperature interval over which the BPs were observed to depend significantly on the molecular structure of the ternary compound. We interpret these observations to suggest that the principal effect of the ternary compounds is to decrease the energy penalty associated with the formation of disclination lines in BPs (and not to change the elastic driving force for BP formation). Overall, these results provide new guidance for tuning the phase stability of BPs. The results also hint at design rules based on the effects of ternary compounds on the stability of defect cores that may find use in LC-based detection technologies that rely on the interaction of the analyte with topological defects in LC systems.

Materials and Methods

Materials.

The nematic LCs MLC-2142 and 4-cyano-4'pentylbiphenyl (5CB), the chiral dopant 4-[[(2S)-2-octanyloxy]carbonyl]phenyl 4-(hexyloxy) benzoate (S-811) and 4-(3-acryloyloxypropyloxy)-benzoic acid 2-methyl-1, 4-phenylene ester (RM257) were purchased from EMD Millipore (Billerica, Mass.). Pyrene was purchased from Thermo Fisher Scientific (Waltham, Mass.). Chloroform, toluene, styrene, o-xylene, 1-butanol, acetonitrile, dichloromethane and isooctane were purchased from Sigma-Aldrich (St. Louis, Mo.), with purity of at least 299%. Analytical standard polystyrene (PS) with $M_n$=1020 was also obtained from Sigma-Aldrich. Silicon wafers were obtained from Silicon Sense (Nashua, N.H.). Glass microscope slides (Fisherfinest™) were obtained from Fischer Scientific (Pittsburgh, Pa.). All materials were used as received.

Preparation of LC Mixtures.

Figure 16:
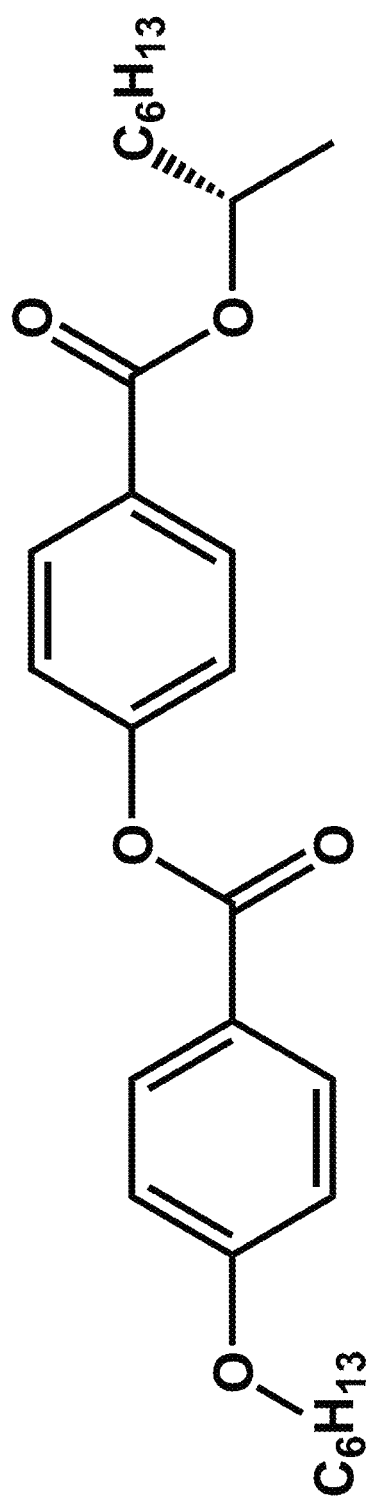
FIG. 16. Chemical structure of 4-[[(2S)-2-octanyloxy]carbonyl]phenyl 4-(hexyloxy) benzoate (S-811) used in Example 4.

Mixtures of the nematic LC MLC-2142 ($T_{NI}$=94° C.) and chiral dopant S-811 were mixed using chloroform as a solvent. For reference, the structure of S-811 is presented in FIG. 16. The mixture was sonicated in a bath of warm water at 70° C. for at least 2 days to allow for the solvent to evaporate. The final concentration of S-811 in the resulting mixture ranged from 5-55% wt/wt. According to the manufacturer, the helical twisting power of S-811 on MLC-2142 is 10.9 µm$^{-1}$, thus 5% to 55% wt/wt S-811 in MLC-2142 provides access to materials with pitches that range from 1.8 µm to 166 nm. To prepare LC mixtures loaded with the ternary compounds (5CB, RM257, pyrene or polystyrene), a solution of the ternary compound in toluene was prepared and added to the cholesteric mixture. The toluene was then evaporated by heating the mixture to 70° C. for at least 1 day.

Fabrication of Microwells.

The LC mixtures were deposited into microfabricated wells with diameters of 200 µm and depths of 22 µm. The details regarding the fabrication of the microwells can be found in the previous chapter.

Optical Characterization of Transition Temperatures.

The phase behaviors of the LC mixtures were determined by heating the samples under a microscope equipped with cross-polars (Olympus bx60, Melville, N.Y.) using a heated stage (Mettler-Toledo, Columbus, Ohio). The temperature treatment of the samples was carried with a heated stage mounted on a microscope. All transition temperatures reported in this paper are those measured upon heating the samples at 0.5° C./min. Previous reports suggest that the transition temperatures of the BP-forming LCs are better characterized upon heating the samples, rather than cooling, in order to avoid ambiguities related to supercooling observed in the transition from the BP into the cholesteric.[11]

Spectroscopic Characterization.

The reflectance spectra of the BP-forming LCs were characterized using a light spectrometer (model F20) from Filmetrics, Inc. (San Diego, Calif.). A 5-µL droplet of the LC mixture was supported onto a clean silicon (Si) wafer. The changes in reflectance of the BP-forming LCs with temperature were characterized by placing the Si-supported LC droplet onto a heated stage and directly under the light path of the spectrometer. The LC droplet was exposed to atmosphere during these experiments and no glass covering was placed between the light source of the spectrometer and the sample.

To characterize the toluene-induced changes in reflectance, the Si-supported LC droplet was place inside the vacuum system described in the previous chapter. The vacuum system had soda-lime glass windows with thickness of 1/16" that separated the sample from the light source of the spectrometer. The quality of the glass was not optical grade and exhibited strong light absorbance in the UV range (<360 nm). As will be discussed later, we hypothesize this effect led to a downward shift on the baseline of the reflectance spectra measured while the LC was inside the vacuum chamber. Nonetheless, the relevant peaks in the reflectance spectra of BP-forming LCs were clearly distinguishable despite these optical artifacts.

Exposure to Toluene Vapors.

The LC mixtures were exposed at room temperature to different volatile compounds using a vacuum system built in-house. Briefly, the BP-forming LC was placed inside the chamber, which was later evacuated to 315 mTorr for ~10 min. Following the introduction of a desired vapor pressure of toluene into the exposure system, the sample LC was equilibrated against the atmosphere of toluene vapor for 2-4 minutes. This equilibration period was sufficient to ensure that the BP-forming LC reached an equilibrium state in the atmosphere of toluene. No changes in the optical properties of the BP-forming LCs were observed with longer equilibration times. The toluene pressure was measured using a Baratron© capacitance manometer (MKS Instruments, Andover, Mass.). Images of the sample exposed to different pressures of the toluene vapor were recorded using a digital camera (Olympus C2040Zoom, Melville, N.Y.).

Results and Discussion

Characterization of Temperature-Dependent Phase Behavior.

In the first set of experiments reported here, we characterized the temperature-dependent phase behavior of LC mixtures prepared using MLC-2142 (nematic LC) and S-811 (chiral dopant). As shown below, the mixtures of S-811 and MLC-2142 formed BPs within temperature ranges that depended on the concentration of chiral dopant. As a representative example, first we discuss the phase behavior and optical characterization of a mixture containing 32.5 wt. % of the chiral dopant. Subsequently, we present the phase diagram for LC mixtures containing 20-55 wt. % of S-811. We note here that the temperature-dependent phase behavior is used as a reference behavior against which we compare the influence of toluene and other small organic molecules (pyrene, etc.)

Figures 17A, 17B, 17C, 17D:
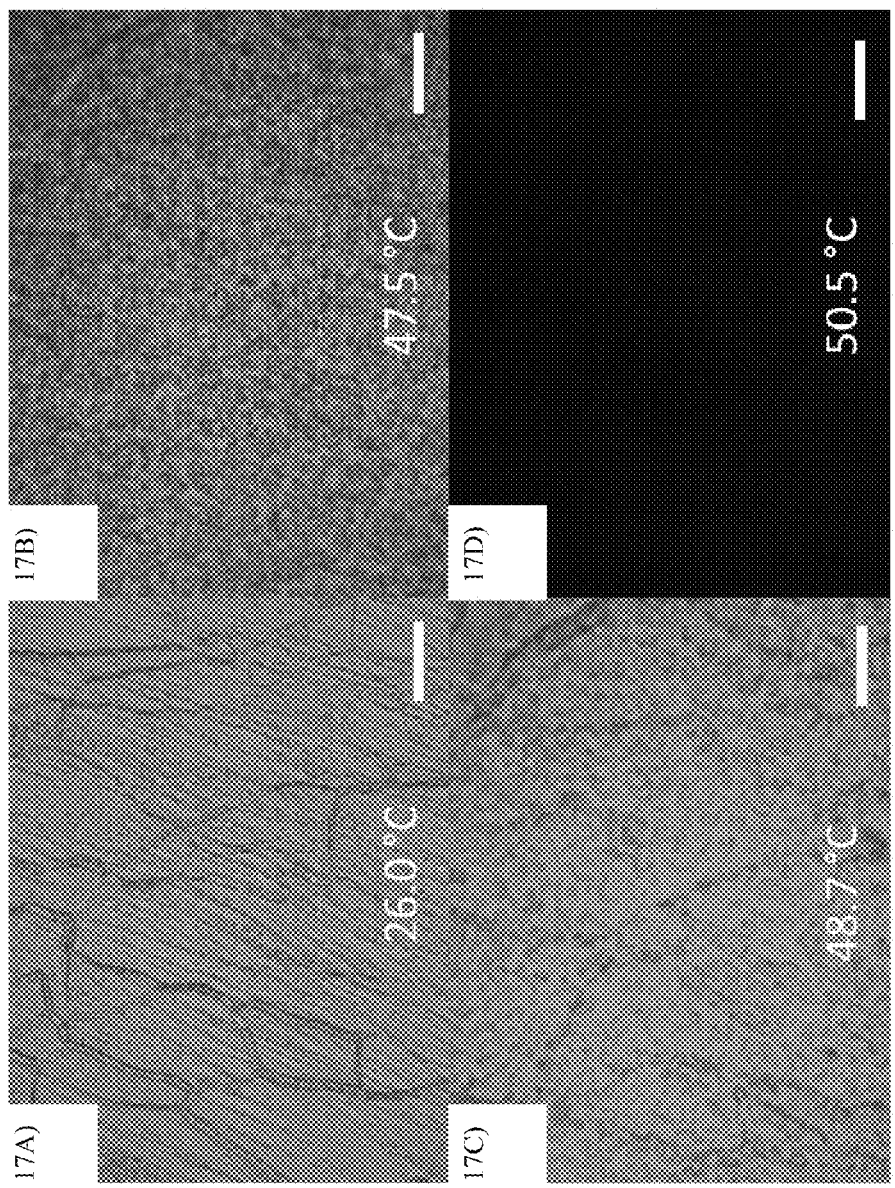
FIGS. 17A-17D. Images of a BP-forming LC containing 32.5 wt. % of S-811 at different temperatures: (17A) 26.0° C. (cholesteric phase); (17B) 47.5° C. (BP I phase); (17C) 48.7° C. (BP II phase); and (17D) 50.5° C. (isotropic phase). Image (17A) was obtained with a crossed-polarized light microscopy using transmitted-light illumination. Images (17B, 17C and 17D) were obtained using reflected-light illumination. Scale bar corresponds to 100 µm.

To characterize the phase behavior of the LC mixture containing 32.5 wt. % of S-811, we placed the LC between two glass slides separated by 18 um thick spacers. The sample was mounted onto a heated stage and observed under a light microscope using crossed-polars. The initial observations of the cholesteric LC were made using transmitted-light and a representative image is shown in FIG. 17A. This image, obtained at room temperature (26.0° C.), shows the characteristic Grangjean texture of a cholesteric with planar anchoring conditions at the top and bottom interfaces with glass. The optical texture of the cholesteric changed little until the temperature was increased to 47.5° C., at which point the sample abruptly lost birefringence and appeared dark when viewed using transmitted light. However, when the sample was imaged using reflected light, brightly colored granular domains with blue and red colors were observed at 47.5° C. (FIG. 17B). This optical texture persisted as the temperature was increased to 48.7° C. At this temperature, a second abrupt change in the optical appearance of the sample occurred and we observed bright-green granular domains (FIG. 17C). Finally, at 50.5° C., we observed the sample to appear dark when viewed with transmitted or reflected light, consistent with an isotropic phase of the material (FIG. 17D).

The sudden changes in appearance of the sample at 47.5° C. and again at 48.7° C. are characteristic of first-order phase transitions in the LC.[6] Moreover, the bright granular texture evident under reflected-light illumination (FIGS. 17B and 17C) is consistent with light (Bragg) reflection from a material composed of a periodic lattice. Past studies have identified two distinct phases that possess periodic cubic structures: BP I (body-centered cubic) and BP II (simple cubic), with BP I more stable relative to BP II at lower temperatures.[3,4] When combined, these observations lead us to conclude that the images presented in FIGS. 17B and 17C correspond to the phases BP I and BP II, respectively. Another phase, BP III, which is characterized by a hazy blue appearance and occurs at higher temperatures than the BP II but below the clearing point, was not observed in this sample. Further evidence that supports the assignment of these phases to BP I and BP II will be presented below in the context of measurements of the reflectance spectrum of the LCs.

Next, we measured the reflectance spectra of the cholesteric LC containing 32.5 wt. % of the chiral dopant at different temperatures. These measurements allowed us to quantify the temperature-dependent changes in the pitch of the cholesteric and to confirm the presence of BP I and BP II at elevated temperatures. A representative spectrum of the BP-forming cholesteric LC at room temperature (26° C.) is presented in FIG. 18A, which shows a single peak at 492 nm. This peak is associated with the Bragg reflection from the helical distortion in the director of the cholesteric LC.[16] The relationship between the pitch of the cholesteric, p, and the measured wavelength of reflection, $\lambda$, is $\lambda = p\bar{n}$, where $\bar{n}$ is the average refractive index of the material.[1]

To calculate the cholesteric pitch from reflectance spectrum, we used the average refractive index of MLC-2142 provided by the manufacturer: $\bar{n}=1.6356$. Using this value, we calculate that the pitch of the cholesteric mixture containing 32.5 wt. % is 301 nm at room temperature. Henceforth, the values of the cholesteric pitch that we report were calculated using the wavelength of maximum reflection obtained from the reflectance spectra and the value of the average refractive index of MLC-2142 provided by the manufacturer.

Figures 18A, 18B:
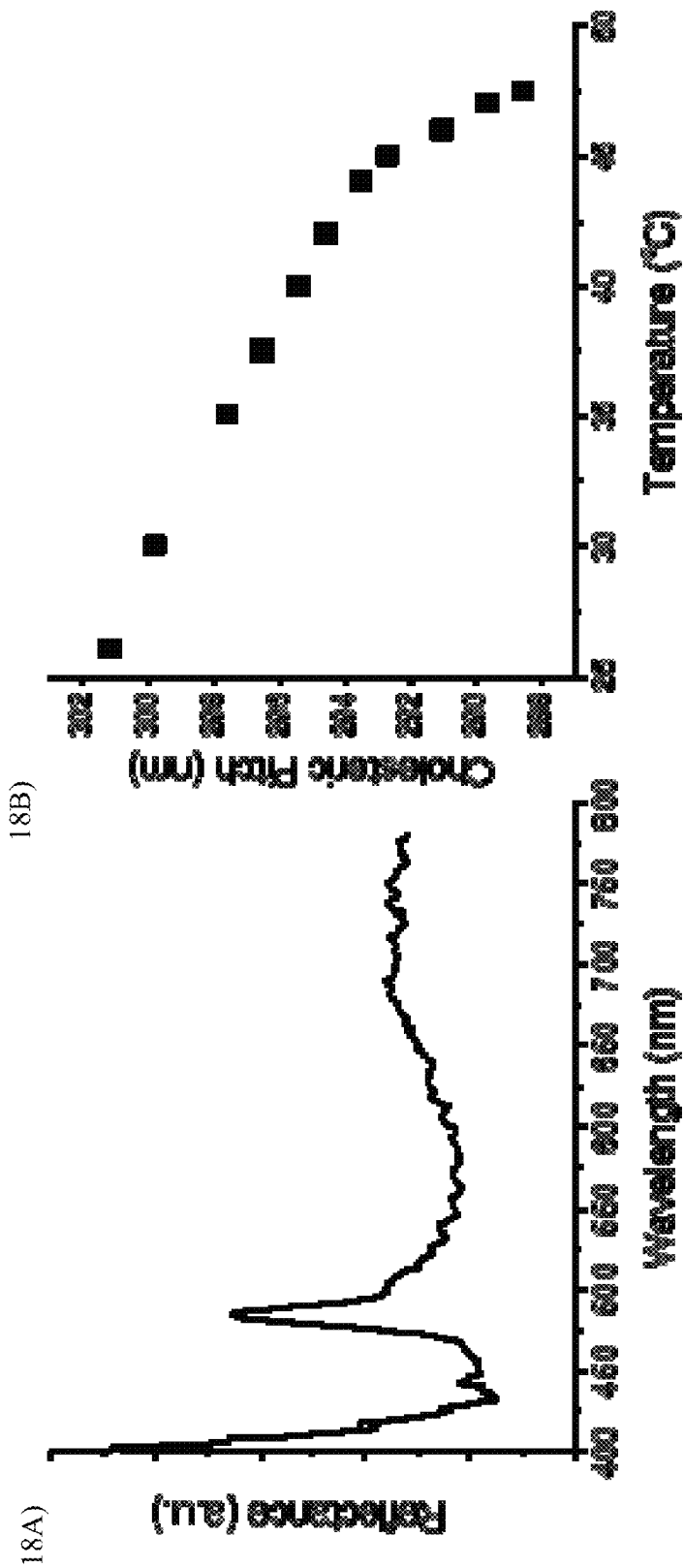
FIGS. 18A-18B. (18A) Reflection spectrum obtained from a BP-forming cholesteric LC (containing 32.5 wt. % of S-811) at room temperature. Peak at 492 nm corresponds to Bragg reflection due to helical distortion of the LC director. (18B) Pitch of helical director in the cholesteric LC as function of temperature.

The temperature-dependent changes in the pitch of the cholesteric mixture containing 32.5 wt. % of S-811 are presented in FIG. 18B. We observed that increasing the temperature of the cholesteric LC led to a decrease in the pitch. At 47.4° C., just below the phase transition into the BP I, the pitch decreased to 288 nm, a change of 13 nm as compared to the room temperature measurement. This temperature-dependent behavior is consistent with previous observations of LC mixtures containing S-811. A past study by Shim et al., for example, reported a cholesteric mixture of ML-0643 (nematic LC from Merck) and S-811 to exhibit a decrease of 70 nm in the pitch as the mixture was heated from 30° C. to 46° C.[17] We note, however, that whether the pitch of a cholesteric LC increases or decreases with temperature depends on the chemical nature of the chiral agent and nematic matrix.[1,17]

To provide further characterization that supports the presence of the BPs in the mixtures used in our study, we measured the reflectance spectra of the cholesteric mixture containing 32.5 wt. % of S-811 at elevated temperatures. The spectra were measured at wavelengths between 400-800 nm, which is the relevant range for characterization of the optical textures presented in FIG. 17. As discussed above, when this mixture was heated between 47.5-48.4° C., we observed granular textures with blue and red domains (FIG. 17B). In this temperature range, the reflectance spectrum of the LC exhibited two peaks characteristic of Bragg diffraction from a periodic lattice.

Figures 19A, 19B:
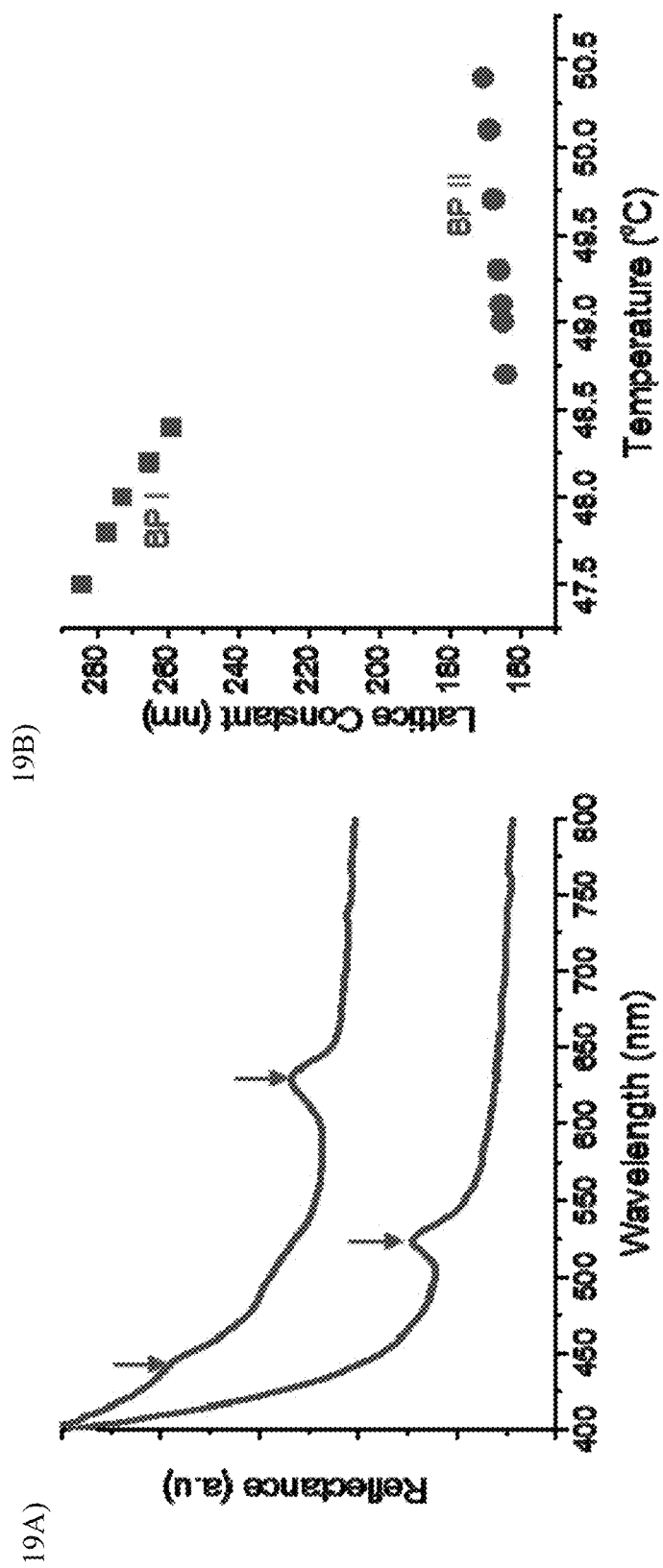
FIGS. 19A-19B. (19A) Reflection spectra of BP-forming LC containing 32.5 wt. % of S-811 at 47.8° C. (red trace) and 48.7° C. (green trace). (19B) Lattice constants of BP I (red squares) and BP II (green circles) as a function of temperature.

As will be discussed below, the positions of the peaks in the reflection spectra depend on the temperature of the sample. At 47.8° C., for example, the peaks appeared at 642 nm and at 454 nm (see FIG. 19A). The ratio of these two wavelengths is 1.41, or $\sqrt{2}$, which characterizes the selection rules for Bragg reflection from body-centered cubic lattices.[4,18] In particular, for BCC structures, the largest reflection wavelength is associated with the (110) planes while the second largest reflection wavelength is associated with the (200) planes.[4] For the BCC lattice, the relationship between the lattice spacing, a, and the reflection wavelength from the (110) plane, $\lambda_{(110)}$ is $a=\lambda_{(110)}/(\bar{n}\sqrt{2})$, where $\bar{n}$ is the average refractive index.[19] Thus, we calculate the lattice spacing for the BCC structure at 47.8° C. to be 278 nm (using $\bar{n}=1.6356$). Since BP I possesses a BCC structure, we conclude that the LC phase observed between 47.5-48.4° C. with 32.5 wt. % of S-811 corresponds to BP I.[4,18,19,16]

At higher temperatures, between 48.5° C. and 50.4° C., we observed the sample to display a granular texture with a uniform green color. Consisted with this color, the reflectance spectrum of the LC exhibited a single peak at 537 nm when heated to 48.7° C. (see FIG. 19A). Because only a single peak is observed in the reflectance spectrum, the structure of the lattice cannot be assigned based on the data presented here. Based on previous reports that identify the phase occurring at higher temperature than BP I as the BP II phase[2,4,18], we follow a similar assignment for the phase observed between 48.7° C. and 50.4° C. BP II is reported to have a simple cubic lattice structure, where the largest reflection wavelength is associated with the (100) plane.[4,18] For the simple cubic lattice of BP II, the lattice spacing can be calculated by the formula $a=\lambda_{(100)}/(2\bar{n})$. Thus, at 48.7° C., we conclude that the lattice spacing of BP II is 164 nm.

By collecting the reflection spectra of the BP I and BP II phases at various temperatures, we observed that the position of the reflection peaks depended on the temperature of the sample containing 32.5 wt. % of S-811. This observation indicates that the spacing of the cubic lattices changed with temperature. The results for the calculated lattice spacing of BP I and BP II, as a function of temperature, are presented in FIG. 19B. Interestingly, we note that the temperature dependence of the lattice spacing is opposite for BP I and BP II. For BP I, the lattice constant decreased from 284 nm at 47.5° C. to 259 nm at 48.4° C.; for BP II, the lattice constant increased linearly from 164 nm at 48.7° C. to 171 nm at 50.4 C. However, we do not yet understand the origin of temperature-dependent these effects on the lattice spacing of BP I and BP II.

Figures 20A, 20B:
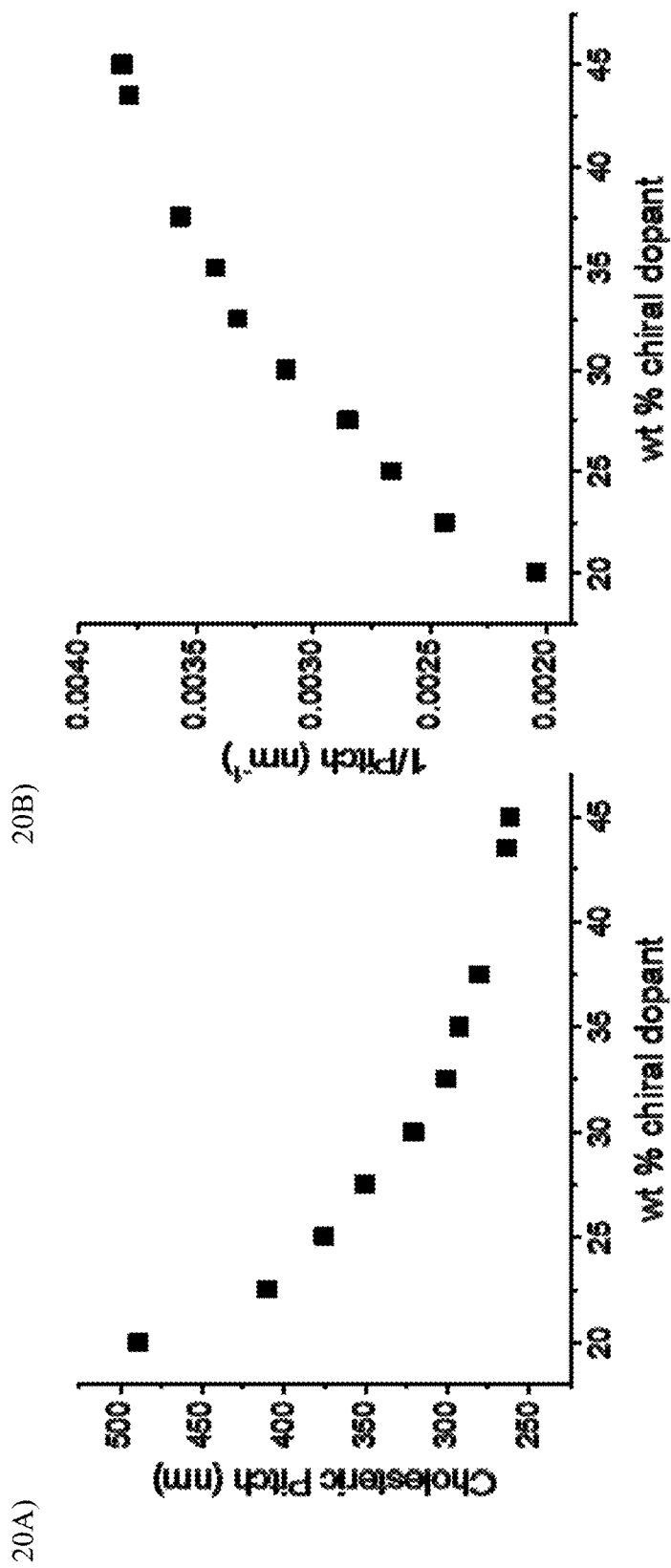
FIGS. 20A-20B. (20A) Pitch of cholesteric LCs as a function of the weight percent of the chiral dopant (S-811). Data obtained at room temperature (26° C.). (20B) Plot of inverse of the pitch against the concentration of chiral dopant in the LC.

Building from the experiments reported above, we next describe the temperature-dependent phase diagram of mixtures of MLC-2142 and S-811 at various concentrations of S-811. First, we characterized the pitch of the cholesteric LC as a function of the concentration of chiral agent in the mixture. As shown in FIG. 20A, the relationship between the concentration of chiral agent in the mixture and the pitch of the resulting cholesteric is non-linear. At 20 wt. % of S-811 the cholesteric has a pitch of 410 nm at room temperature; however, a mixture containing 45 wt. % of the chiral agent had a pitch of 262 nm. As described below, only mixtures containing 25.0 wt. % or more of the chiral agent exhibited a BP. These mixtures had a pitch of 375 nm (for 25 wt. % S-811) or less at room temperature. Though it is commonly reported that the pitch of the cholesteric is inversely related to the concentration of chiral agent in the mixture, our mixture did not follow this relationship.[1] As shown in FIG. 20B, the data of the inverse pitch against the weight fraction of chiral dopant exhibits a deviation from the expected linear behavior.

Next, the phase behavior of the LC mixtures containing S-811 at concentrations between 20-55 wt. % was investigated by heating these mixtures to elevated temperatures and observing the phase transitions using optical microscopy (reflection-mode; crossed-polars). BP I was assigned as the first phase that appeared upon heating the cholesteric to elevated temperatures and observing a first order phase transition. BP II was assigned as the phase that appeared upon heating the BP I at elevated temperatures and observing a first order phase transition. The assignment of BP III was facilitated by the fact that these phases exhibit a characteristic blue haze. In summary, the temperature-dependent phase diagram of mixtures of MLC-2142 and S-811 is presented in FIG. 21A.

Figures 21A, 21B:
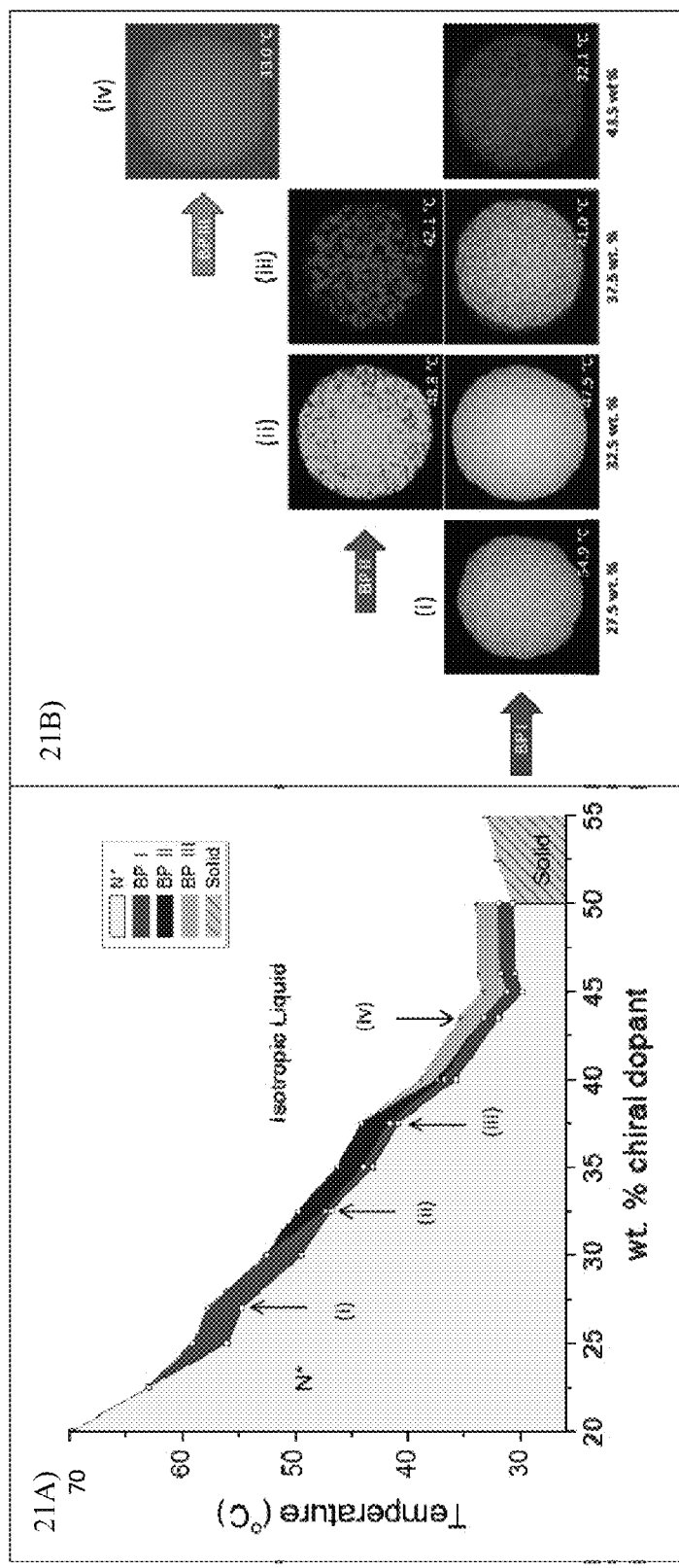
FIGS. 21A-21B. (21A) Temperature-dependent phase diagram of BP-forming LCs containing S-811 (chiral dopant) and MLC-2142. The label N* corresponds to the cholesteric phase. The arrows indicate the phase behavior of selected mixtures containing various concentrations of the chiral dopant: (i) 27.5 wt. %; (ii) 32.5 wt. %; (iii) 37.5 wt. %; and (iv) 43.5 wt. %. Images of the various BP textures for these selected mixtures are presented in (21B). The composition of the corresponding LC mixture is shown at the bottom of each column. The temperature at which each texture is observed is marked at the lower right corner of each image. At the left of each row the label designating the type of BP (BP I, BP II or BP III) is shown with an arrow. Images obtained by crossed polarized microscopy using a 50× magnification objective and reflected-light illumination. LC films (supported on microwells) had a diameter of 200 µm and a thickness of 22 µm.

For mixtures of MLC-2142 and S-811 containing concentrations of 22.5 wt % or less of S-811, we observed a room-temperature cholesteric phase and a cholesteric to isotropic phase transition upon heating the mixture to sufficiently high temperatures. In contrast, mixtures containing 25.0-50.0 wt. % S-811 exhibited one or more BPs upon heating to elevated temperatures. The transition temperatures and the optical properties of the BPs were dependent on the compositions of the mixtures. In FIG. 21B, we present images of the various BPs observed at different compositions. The mixtures containing S-811 at concentrations of 25.0 wt. % to 30 wt. % only exhibited a BP I upon heating to elevated temperatures. For example, the cholesteric mixture containing 27.5 wt. % of the chiral dopant transitioned into BP 1 at 54.9° C.

Upon imaging the mixture under reflection-mode, we observed a texture with green granular domains (See FIG. 21B(i)). Increasing the temperature of the BP I up to 57.8° C. did not lead to significant changes in the observed texture of the sample. Above 57.8° C., however, we observed that the granular domains began to melt into the isotropic phase.

BP I was observed for all of the mixtures containing 25.0-50.0 wt. % S-811, although its optical appearance was different depending on the concentration of S-811. For example, in a mixture containing 32.5 wt. % of S-811, the BP I exhibits red and blue granular domains (FIG. 21B(ii)). However, in a mixture containing 43.5 wt. % of S-811, the BP I appears blue with a granular structure (FIG. 21B (iii)). We attribute these optical differences to the different lattice spacing of the BP I that arise through changes in the concentration S-811. As noted above, increasing the concentration of S-811 in the cholesteric mixture leads to a decrease in the pitch of the cholesteric. Similarly, we hypothesize that the lattice spacing of BP I decreases with increasing concentrations of S-811.

The BP II was observed for mixtures with 32.5-40 wt. % of the chiral dopant S-811 at higher temperatures than the BP I. As explained earlier, the BP II was characterized by the sudden change in the optical textures and colors of the sample that are observed when the BP I was further heated to higher temperatures. For example, the sample containing 32.5 wt. % S-811, whose BP I had red and blue granular domains, transitioned abruptly at 48.7° C. to a texture with bright green and blue granular domains. At temperatures ~2° C. higher than the BP I-to-BP II transition temperature, the colored domains of the BP II began to melt into the isotropic phase.

Mixtures containing 40.0-50.0 wt. % of the chiral dopant exhibited a hazy blue appearance at higher temperatures than the BP II or BP I but below the clearing point, consistent with descriptions of the so-called BP III (see FIG. 21B(iv)). We note that only the mixture containing 40.0 wt. % of S-811 exhibited all three BPs (BP I, BP II and BP III) as a function of increasing temperature. LC mixtures with higher concentrations of S-811 only displayed a transition from BP I directly to BP III at higher temperature. BP III was only observed in a temperature window of ~2° C. below the temperature for transition into the isotropic phase.

Samples with concentrations >50 wt. % were solid and did not exhibit a LC phase upon heating to high temperatures. These samples appeared to melt into an isotropic liquid at temperatures above 30° C.

Toluene-Induced Phase Transitions in BPs.

The results presented above, which characterized the temperature dependent phase behavior, are used to guide the design of experiments aimed at understanding the effects of toluene in the LC phase diagram. In the next set of experiments, we characterized the optical response of the BP-forming LCs when exposed to different vapor pressures of toluene. As a representative example, we present the results obtained for a mixture containing 32.5 wt. % of the S-811 chiral dopant. Before exposing to toluene, consistent with FIG. 17, the sample had a N*-to-BP I transition at 47.5° C., a BP I-to-BP II transition at 48.7° C. and a BP II-to-isotropic transition at 50.5° C. This sample did not exhibit a BP III phase upon heating.

Figure 22:
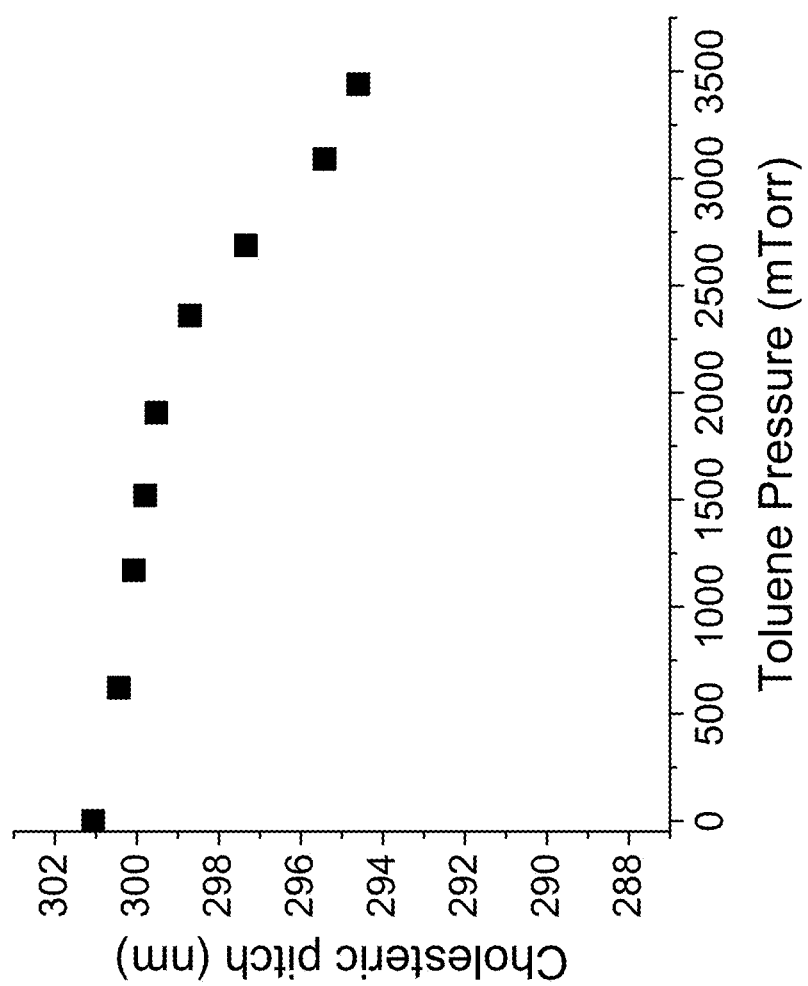
FIG. 22. Pitch of BP-forming cholesteric LC as a function of toluene pressure. The measurements were carried at room temperature (26° C.).

At room temperature and prior to exposure to toluene, the characteristic cholesteric texture was readily observed when the sample was viewed under crossed polarizers. As noted previously, at room temperature and prior to exposure to toluene this LC mixture exhibited a (Bragg) reflection peak at 492 nm, which corresponds to a cholesteric pitch of 301 nm. This optical signature did not change significantly as the sample was exposed to pressures of toluene up to 3500 mTorr. Consistent with this visual observation, the pitch of the cholesteric decreased by only 7 nm, to 294 nm, after the sample was exposed to 3500 mTorr of toluene (FIG. 22).

We note that this result is surprising in light of previous work that reports a significant increase in the pitch of a cholesteric LC exposed to vapors of small molecules.[12-15] In the work by Chang et al., for example, the pitch of a cholesteric formed by a mixture of E7 (nematic LC) and 17 wt % and 2 wt. % of the chiral dopants S-1011 and DBD, respectively, was reported to increase by over 130 nm as the LC saturated with toluene (in their work, the concentration of toluene required to saturate the LC was not reported).[14] Also, the authors do not report whether the cholesteric mixtures used in their work form BPs at elevated temperatures. We hypothesize that the difference in chemical structure of the materials used here and in previous reports to form cholesteric LCs accounts for the observed differences in the behavior of the pitch when the LCs are exposed to vapors of small molecules such as toluene.

Figures 23A, 23B, 23C, 23D:
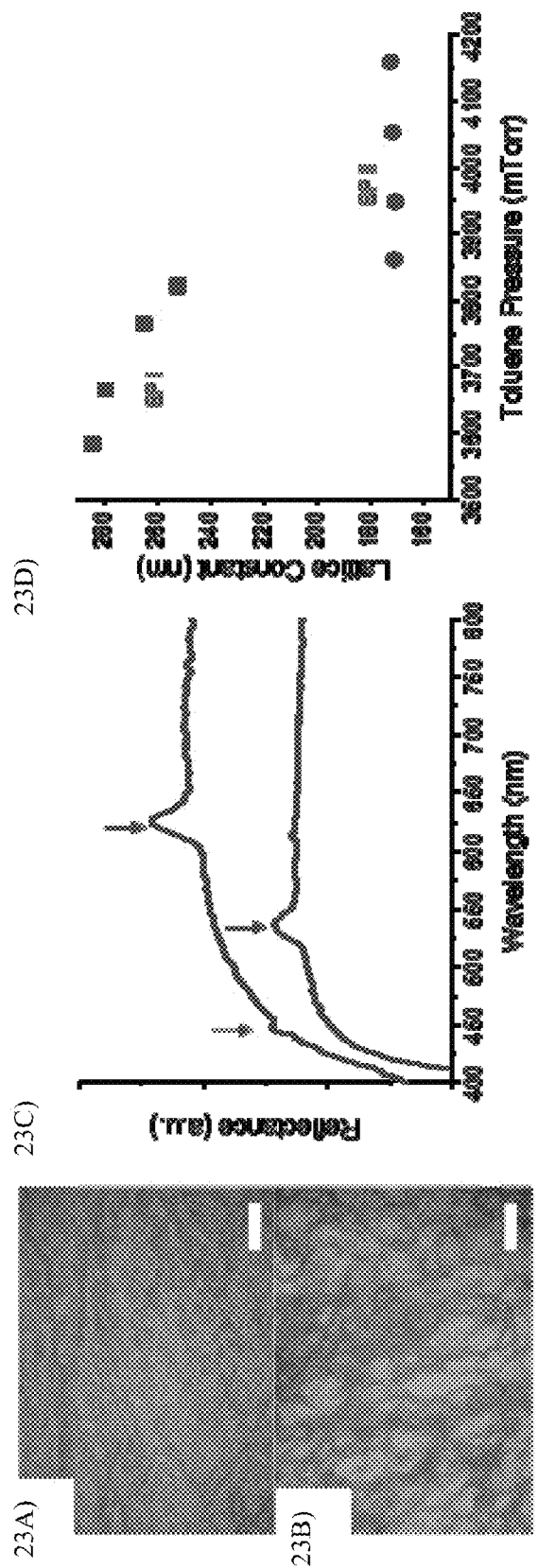
FIGS. 23A-23D. Images of BP-forming LC at 26.0° C. and exposed to vapors of toluene at different pressures: (23A) 3580 mTorr and (23B) 3860 mTorr. Images obtained with a crossed-polarized light microscopy using reflected-light illumination. Scale bar corresponds to 100 µm. (23C) Reflectance spectra of BP-forming LC exposed to vapors of toluene: 3760 mTorr (top trace) and 3860 mTorr (bottom trace). (23D) Lattice constants of BP I (squares) and BP II (circles).

As the LC containing 32.5 wt. % of the chiral dopant was exposed to 3580 mTorr of toluene at room temperature, we observed the sample to abruptly lose birefringence and appear dark when viewed using a cross-polarized light microscope under transmission-mode illumination. However, when imaging under reflection-mode illumination, brightly colored granular domains with red and blue hues were observed to form (FIG. 23A). A further increase in the toluene pressure led only to a decrease in the intensity of light reflected from the image, without any modification to the overall colors or morphology of the sample. However, a second abrupt change in appearance of the sample occurred at 3860 mTorr of toluene vapor (FIG. 23B). In this case, the red and blue domains shown in FIG. 23A suddenly disappeared to give rise to granular, green domains. This green appearance of the sample was maintained until 4200 mTorr, when the granular domains began melting into the isotropic phase. These abrupt changes in the optical appearance of the LC at a particular value of the vapor pressure of toluene are consistent with toluene-induced first-order phase transitions. We hypothesized that the phases reported in FIGS. 23A and 23B correspond to BP I and BP II, respectively.

To confirm the identity of the above-described phases observed at high vapor pressures of toluene, we measured the reflection spectrum of the LCs in the range of wavelengths between 400-800 nm. The spectra of the LC exposed to toluene at pressures between 3580-3820 mTorr exhibited two peaks consistent with Bragg diffraction from a periodic lattice. At 3760 mTorr, for example, the maxima are located at 624 nm and 445 nm (see FIG. 23C). The ratio between the two wavelengths is 1.41, or $\sqrt{2}$, consistent with the selection rules for Bragg reflection from the BCC structure found in BP I. When the LC was exposed to toluene pressures between 3860-4200 mTorr, the spectra of the LC exhibited a single peak. At 3860 mTorr of toluene, for example, the peak occurs at a wavelength of 534 nm (FIG. 23C), consistent with BP II (see above).

We note that the wavelength at maximum reflectance for the toluene-induced BP 1 and BP II depended on the pressure of toluene at which the LC sample was exposed. This behavior is consistent with a change in the lattice spacing induced by toluene vapors. The lattice constants for BP I and BP II as a function of toluene pressure are presented in FIG. 23D. For BP I, the lattice spacing decreases non-linearly from 284 nm to 252 nm as the pressure of toluene increases from 3580 mTorr to 3820 mTorr. This behavior is similar to the temperature-dependent change in lattice spacing presented in FIG. 19B. For BP II, however, the lattice spacing changes by 2 nm, from 171 nm to 173 nm, over the range of toluene pressure at which BP II is observed.

We hypothesize that the decrease of the spectral baseline in FIG. 23C at low wavelengths is due to the optical artifacts induced by the thick glass plate placed between the LC mixture and the reflectometer. This glass plate is part of the vacuum system in which the LC is enclosed.

Figure 24:
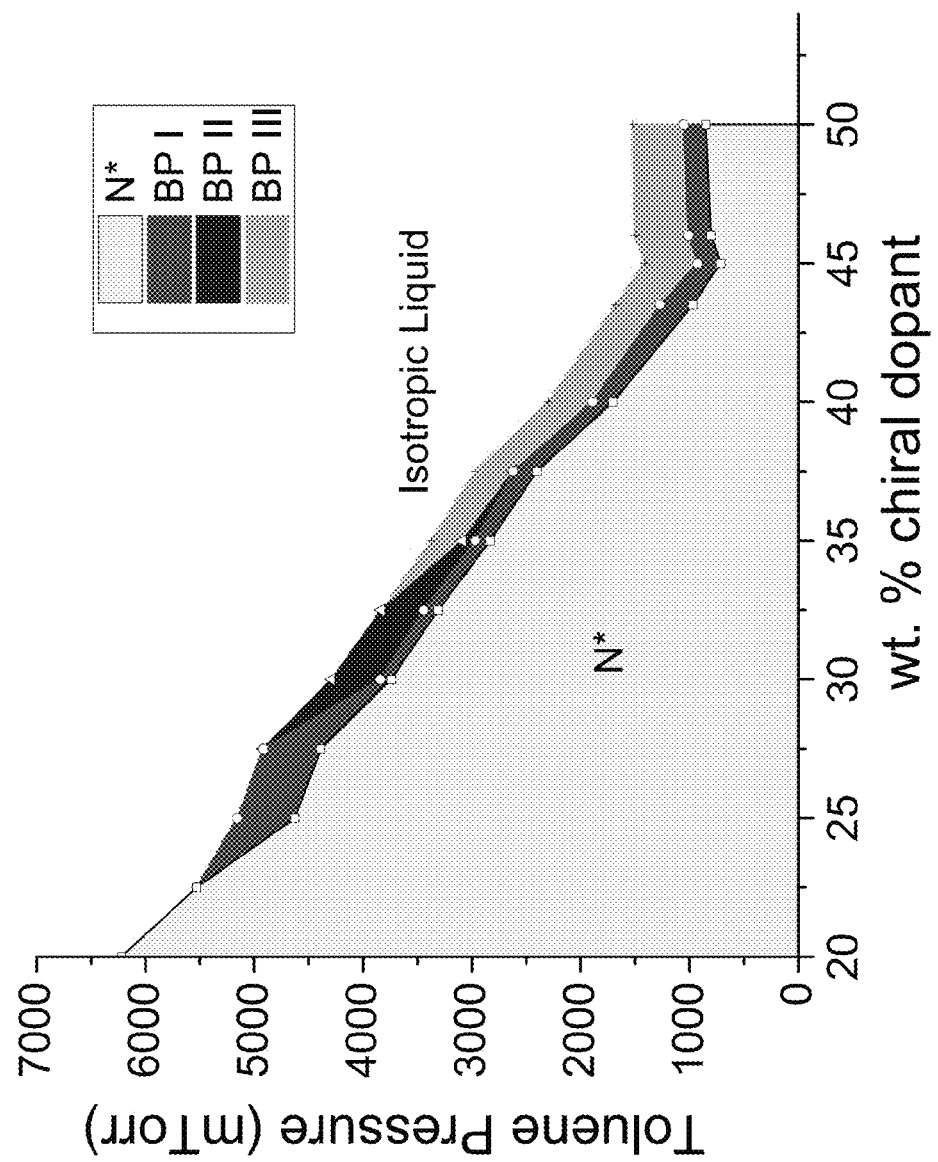
FIG. 24. Phase diagram of transitions induced by different concentrations of toluene vapors at which the LC samples were exposed to at room temperature (26° C.).

Following characterization of the LC mixture with 32.5 wt. % chiral dopant, we proceeded to study the effect of chiral dopant concentration on the amount of toluene required to induce each phase transition (FIG. 24). We found that mixtures containing 22.5 wt. % oR less of the chiral dopant did not exhibit a BP when exposed to toluene. Similar to the results presented with the temperature-dependent phase behavior, only samples containing S-811 concentrations between 25.0-50.0 wt. % exhibited a BP when exposed to toluene.

We measured the pressure of toluene required to induce the phase transitions of the samples to be highly sensitive to the weight percent of chiral dopant (FIG. 24). Going from 25.0 wt. % to 45.0 wt. %, the pressure of toluene required for the cholesteric-to-BP I transition decreased more than six-fold, from 4620 mTorr to 720 mTorr. The vapor pressures of toluene needed to induce BP 11 or BP III phases also decreased with increasing concentration of S-811. However, using concentrations of S-811 higher than 45 wt. % did not lead to further reductions in the toluene pressure required for phase transition. The sample with 35 wt. % S-811 was the only one that exhibited all three BPs at various pressures of toluene. Mixtures with 32.5 wt. % S-811 only exhibited BP I and BP II when exposed to toluene. In contrast, samples with concentrations of 37.5 wt % and above did not exhibit a BP II, only BP I and BP III were observed in these samples. This result is consistent with previous literature that reports that BP II is unstable for high chirality mixtures.[2] Mixtures with concentrations above 50 wt. % of S-811 were solid at room temperature and did not exhibit a LC phase upon exposure to toluene.

As discussed in the Introduction to this example, elastic effects favor the formation of double-twist cylinders over the single-twist helical distortion of the cholesteric phase. As we will explain in the Discussion section of this example, the cholesteric pitch influences the elastic energy of the LC. In light of previous literature that highlights an increase of the pitch of a cholesteric[12-15], we predicted that the addition of toluene to a BP-forming cholesteric would lead to a transition into the isotropic phase directly, inhibiting the formation of the BPs by decreasing the elastic effects in the LC. Thus, the toluene induced phase transition into the BPs presented here, even for cholesteric mixtures having a relatively low concentration of chiral dopant (25.0 wt. % S-811), is surprising.

In contrast to previous reports, our experiments indicate that the addition of toluene to BP-forming cholesteric LCs leads to a small decrease in the pitch of 7 nm even after the sample was exposed to 3500 mTorr of toluene. The observed cholesteric-to-BP transition in the presence of toluene, instead, supports the hypothesis that the primary effect of toluene is to decrease the energy penalty associated with the formation of disclination cores of the BPs. Although our data does not preclude that toluene might also change the magnitude of the elastic constants, our results demonstrate that the effects of toluene on energetics of the formation of disclination cores dominate (the pitch changes little when the cholesteric is exposed to toluene vapors). We hypothesize that once the energy barrier for the formation of disclination lines is low enough, the release in elastic energy made possible by the formation of the double twist structures leads to the formation of the BP. This model points to the cholesteric LC as an elastically strained phase which relaxes into the double twist cylinders upon lowering of the energy penalty associated with the creation of the disclination cores.

We propose two explanations to account for the mechanism by which toluene decreases the energy associated with the creation of disclination cores and enables the formation of BPs at low temperatures: (1) similar to the studies of polymer- or nanoparticle-loaded BPs[7-10], one possibility is that toluene partitions preferentially into the volume occupied by the disclination cores of the BP, replacing with toluene the regions in which the mesogen has a decreased local order; (2) the second hypothesis is that toluene mixes uniformly in the LC and leads to a decrease in the order-disorder transition of the LC mixture. These two hypotheses could be probed experimentally by characterizing the phase transition temperatures of BP-forming LCs loaded with toluene at various concentrations.

As reported in the literature, stabilization of the BP via replacement of the regions of the disclination cores by polymers of nanoparticles is evidenced by an increase in the temperature range over which the BPs are observed.[7-10] Similarly, if toluene partitions preferentially to the disclination cores, we expect that BP-forming LCs loaded with toluene exhibit an increased temperature range over which the BPs appear, in comparison with BPs that do not contain toluene. Alternatively, if toluene mixes uniformly in the LC mixture, we do not expect to see a change in the temperature interval over which the BPs appear. In this case the order-disorder transition temperature is expected to decrease, bringing the phase transition temperatures for the BPs to lower temperatures.

We attempted to characterize the temperature-dependent phase behavior of BP-forming LCs loaded with toluene. Several experiments were attempted, including containing toluene-loaded LC between two glass slides sealed with tape. However, we found that toluene quickly evaporated from the LCs, making it difficult to obtain a mixture with a known and stable concentration of toluene. Instead, as will be detailed in the following section, we mixed small non-volatile molecules on BP to attempt to replicate the effects of toluene on the phase behavior of the BPs.

Effect of Ternary Compounds on Phase Behavior of BPs.

Figures 25A, 25B, 25C, 25D:
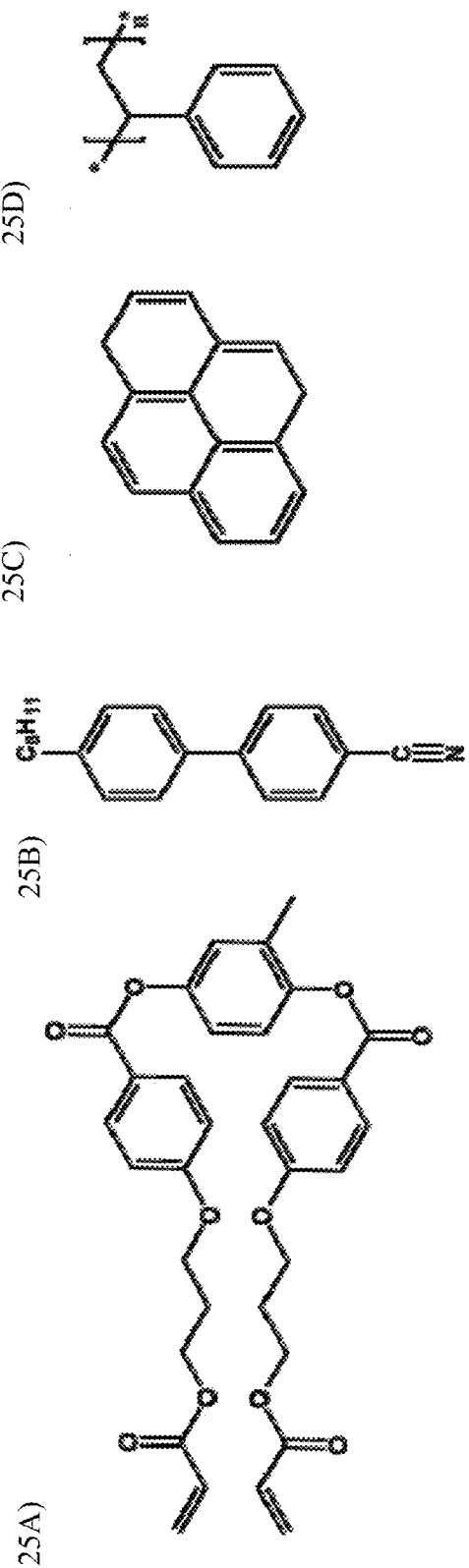
FIGS. 25A-25D. Structures of molecules used in Example 4: (25A) RM257, (25B) 5CB, (25C) pyrene, and (25D) polystyrene (PS) with $M_n$=1020.

In the next set of experiments, we report the effect on the phase behavior of adding structurally distinct non-volatile ternary compounds to BP-forming samples. As noted above, the results presented in this section advance our understanding the toluene-induced phase transitions discussed above. For reference, we used the LC sample containing 32.5 wt. % of S-811 and added to the sample 1 wt. % of RM257, 5CB, pyrene or polystyrene (PS). The chemical structures of these compounds are found in FIG. 25. We selected these compounds based on their different chemical structures and phase behavior. RM257 is also a mesogen, forming a solid at room temperature that transitions to a nematic at 67° C. and to an isotropic liquid at 127° C. 5CB is a mesogen that forms nematic LC at room temperature with a clearing point of 35° C. At room temperature, pyrene is a solid with melting point of 145° C. PS is a viscous liquid. The ternary mixtures containing the cholesteric and 1 wt. % of the different additives were heated until the phase transition into the BPs, and subsequently the isotropic phase, was observed.

Except for PS, we cannot predict a priori what effect these different molecules will have on the phase behavior of the BPs. A previous study by Kasch et al. reports that BPs containing PS exhibit an increased temperature stability.[11] Because the molecular structures of toluene and pyrene have closer resemblance (they are both small aromatic compounds) than the other molecules, we expect that the effect of toluene on the phase behavior of the BP will be most closely replicated by pyrene.

For convenience, we remind the reader that the binary mixture (without ternary compounds) of 32.5 wt. % S-811 in MLC-2142 exhibited a N*-BP I transition at 47.5° C., a BP I-to-BP II transition at 48.5° C. and a BP II-to-isotropic transition at 50.5° C. The temperature range over which the BPs were observed was 3.0° C.

Figure 26:
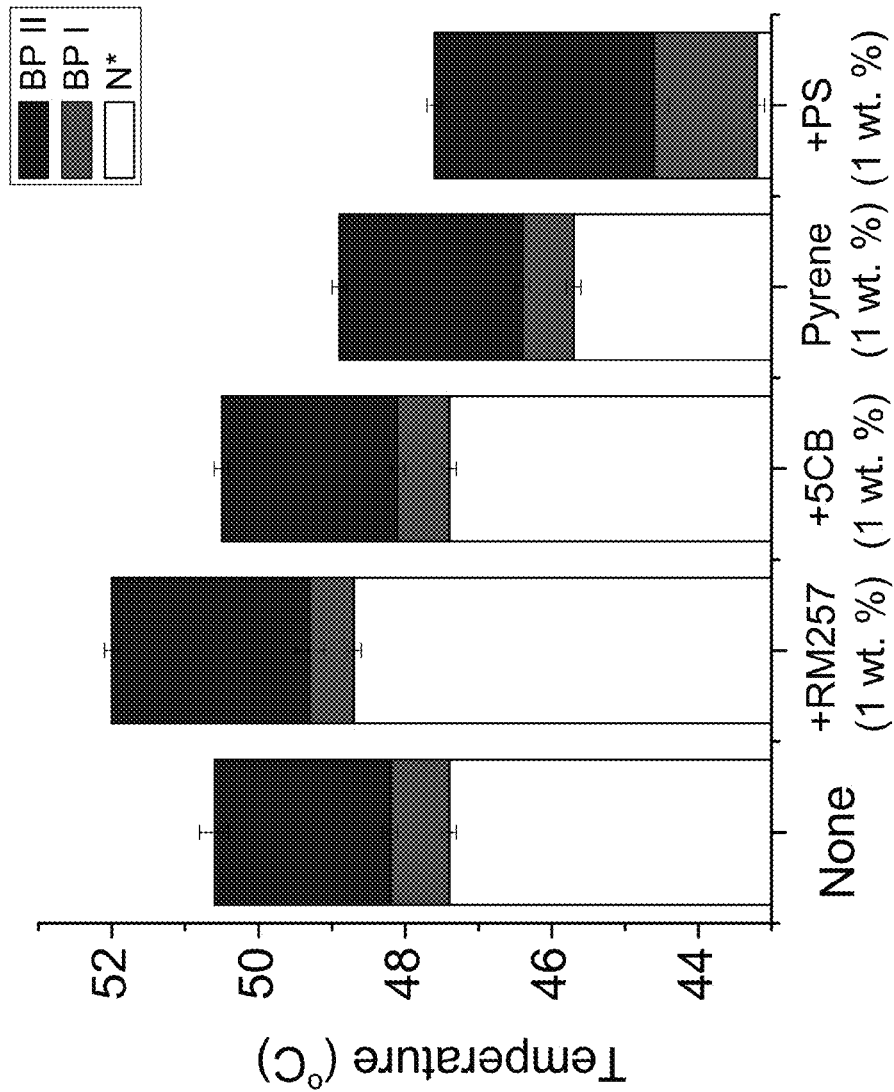
FIG. 26. Effect of guest compound on the phase transition temperatures of the LC containing 32.5 wt. % of the chiral dopant. The addition of RM257 shifted up the temperature range over which the BP is stable while 5CB did not have an effect on the phase transition temperatures of the material. In contrast, pyrene shifted the temperature range of the BP to lower temperatures. The addition of PS led to an increase in the temperature range over which the BPs were observed.
Figure 27:
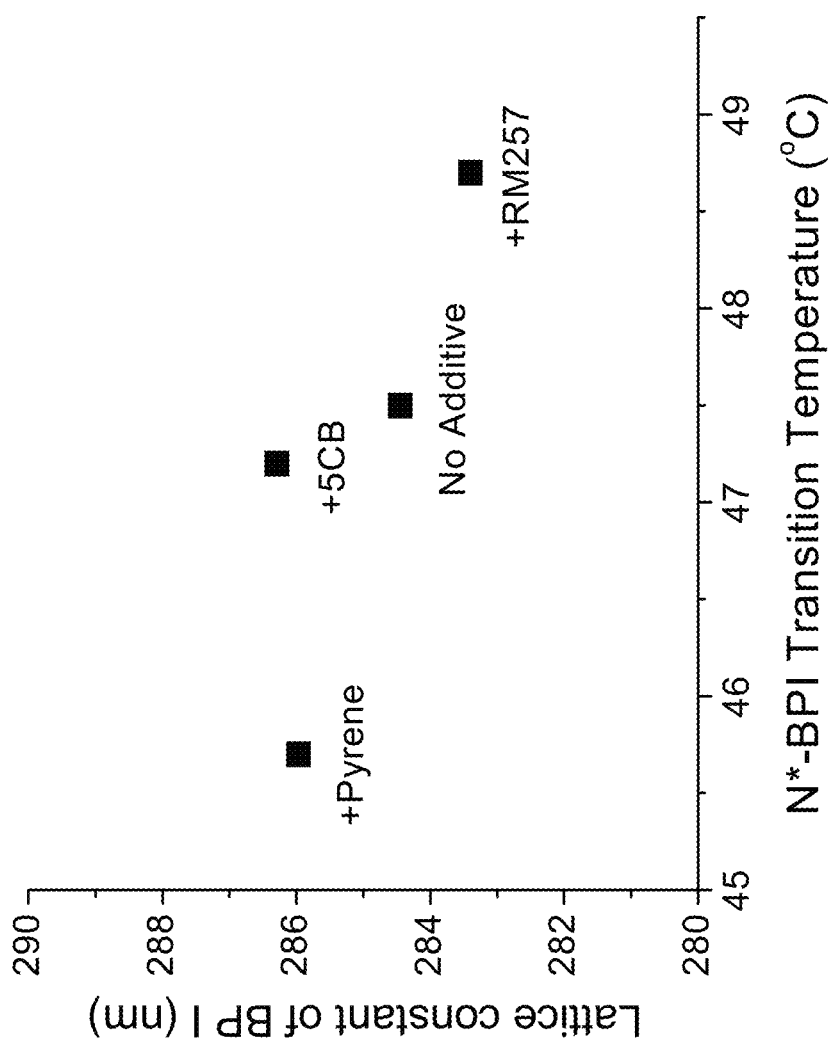
FIG. 27. Lattice constant of BP I at the N*-BP I transition temperature of BPs I wt. % of containing various additives.

Four distinct behaviors were observed depending on the chemical identity of the ternary compound (FIG. 26A): (1) the addition of 5CB did not change the phase behavior of this mixture, both the temperature range and the temperatures at which the BPs were observed remained the same. (2) The addition of RM257 shifted the temperature range of the BPs to higher temperatures, with the BP I, BP II and isotropic phases appearing at 48.7° C., 49.3° C. and 51.7° C., respectively. (3) The addition of pyrene shifted the temperature range to lower values (BP I: 45.7° C., BP II: 46.4° C., iso: 48.9° C.). (4) The addition of PS to the LC mixtures shifted the temperature range of the BPs to lower values but also led to an increase in the temperature range over which the BPs were observed. For this mixture, the BP I appeared at 43.2° C., BP II appeared at 44.6° C., and the isotropic phase was observed at 47.6° C. The temperature range of the BPs containing 1 wt. % PS is 4.4° C., compared with 3.0° C. for BPs containing no ternary compounds, or 1 wt. % RM257, pyrene, or 5CB. This widening of the temperature stability of the BP due to the addition of PS has been previously reported.[11] As discussed earlier, the increased temperature range of the BPs is attributed to the preferential partitioning of the PS into the disclination cores of the BP. Note, however, that the temperature range over which the BPs were observed was unchanged by the addition of RM257 or pyrene to the LC mixture. From these experiments, we conclude that the chemical structure of the molecules added to the BP-forming LC influences the phase behavior of the LC mixture. We hypothesize that RM257 and pyrene change the temperature at which the order-disorder (isotropic) transition is observed in the BP-forming LCs. Because the temperature intervals at which the BPs were observed remained unchanged with the addition of RM257, 5CB or pyrene, we interpret our results to indicate these compounds that do not partition preferentially to the regions occupied by the defect cores of the BPs.

Next, we used reflectometry to characterize the lattice parameters of the BPs containing the ternary compounds described above (concentration of 1 wt. %). The lattice spacings for these mixtures were characterized according to the methods presented above. Although the addition of pyrene or RM257 to the BP-forming LC affected the transition temperature at which the BPs were observed, the lattice spacing was not significantly changed by the addition of ternary compounds. In FIG. 14, we present the lattice constant of BP I for the different LC mixtures (containing ternary compounds) plotted at the temperature at which the cholesteric-BP I transition was observed. For the mixture without additives, the cholesteric to BP I transition occurred at 47.5° C., and at this temperature the lattice spacing of BP I was measured to be 284 nm. For the mixture containing pyrene, the lattice spacing was 286 nm at the phase transition, while for the BP I containing RM257 the lattice spacing was 283 nm at the transition temperature. We note that the differences in lattice constants for these BPs are relatively modest compared to the effect of the ternary compounds on the transition temperatures of the BPs. These results indicate that ternary compounds do not significantly change the lattice constant of BP I.

To further explore the effects of ternary additives on the phase behavior BP-forming LCs, we studied a cholesteric LC containing high concentrations of RM257 or pyrene. These two compounds were selected because they change the order-disorder temperature (clearing point) of the BP-forming LCs in opposite directions without changing the temperature range over which the BPs are observed (See FIG. 26). Pyrene decreases this transition temperature while RM257 increases it. We used a cholesteric LC films containing 0.3 wt. % of S-811 in MLC2142 and various amounts of pyrene or RM257 (up to 15 wt. %). The LC films were sandwiched between two glass slides coated with dimethyloctadecyl[3-(trimethoxysilyl)propyl]ammonium chloride (DMOAP), which induces homeotropic alignment of the LC.

Figures 28A, 28B:
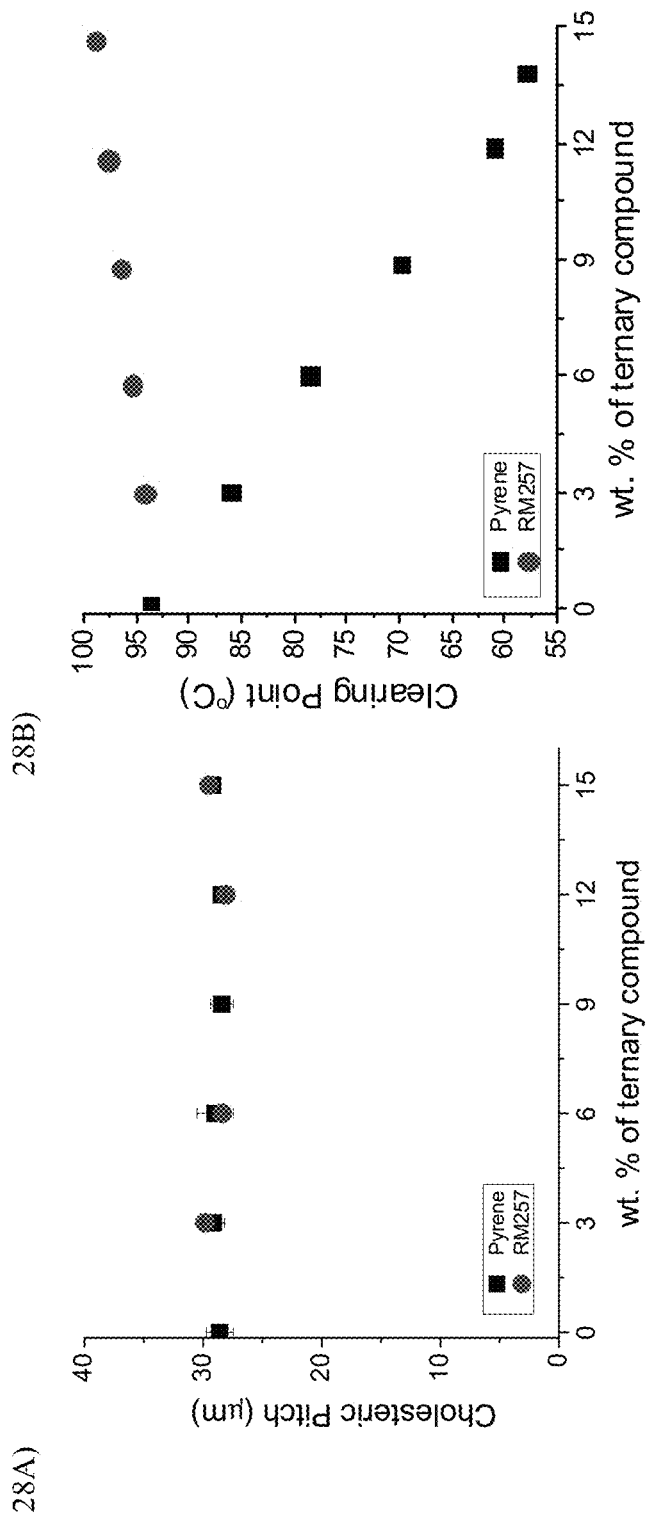
FIGS. 28A-28B. (28A) Pitch and (28B) clearing point of a cholesteric LC containing various amounts of pyrene or RM257. Cholesteric LC contained 0.3 wt. % of S-811. Characterization of the pitch was performed at room temperature.

The fingerprint texture, visible when the LC film was observed under the microscope, was used to calculate the pitch of the cholesteric at room temperature. Without any ternary component, the cholesteric had a pitch of 28 µm and a clearing point temperature of 94° C. As summarized in FIG. 28A, adding RM257 or pyrene to the cholesteric did not have a significant effect on the pitch. All the mixtures exhibited a finger print texture with pitch of ~28 µm, regardless of the concentration of RM257 or pyrene used. In contrast, the change in the clearing point temperature of the mixtures changed dramatically with the addition of the ternary compounds (FIG. 28B). Adding pyrene decreased the clearing point temperature linearly (~2.7° C./wt. % of pyrene). At ~14 wt. % of pyrene in the cholesteric, for example, the clearing point temperature of the mixture had decreased by 40%, from 94° C. to 58° C. RM257 had the opposite effect on the clearing point temperature, which increased by ~0.37° C./wt. % of RM257. Adding 15 wt. % of RM257 to the cholesteric led to a 5% increase in the clearing point temperature, from 94° C. to 99° C. These results demonstrate that the main effect of the ternary compounds on the LC is to change the temperature at which order-disorder transition occurs.

Discussion

In this section, we discuss our experimental observations in the context of the models for the formation of BPs presented in the literature. The goal of this section is to understand how adding ternary compounds affects the energy of formation of BPs. The total free energy of a LC is $F_T = \int (f_{bulk} + f_{el}) dV$, where $f_{bulk}$ and $f_{el}$ are the bulk and elastic free energy density, respectively. The term $f_{bulk}$ accounts for the relative thermodynamic stability of the ordered anisotropic phase over the disordered isotropic phase; the term $f_{el}$ accounts for the increase in energy density due to distortions of the LC director. The free energy of a LC can be described in terms of a tensor order parameter, Q. As described by Wright and Mermin, the equations for $f_{bulk}$ and $f_{el}$ have the following form[20]:

$$f_{bulk} = a(T-T_{iso})tr(Q^2) - btr(Q^3) + c[tr(Q^2)]^2 \quad (1)$$

$$f_{el} = \tfrac{1}{4}K_1[(\nabla \times Q)_{ij} + (q_0 Q_{ij})]^2 + \tfrac{1}{4}K_0[(\nabla \cdot Q)_i]^2 \quad (2)$$

where Q is the tensor order parameter, a, b and c are scalar constants, tr is the trace operation, T is the experimental temperature, $T_{iso}$ is the temperature at which the material transitions into the isotropic phase, $K_1$ and $K_0$ are the elastic constant of the LC and $q_0$ is related to the pitch, $p_0$, by the following equation: $q_0 = 2\pi/p_0$. Local minimization of $f_{el}$, with respect to Q, favors the formation of double twist structures. However, accommodating the double-twist cylinders requires the formation of disclination lines, which contain LC material with low order. At temperature well below $T_{iso}$, the term $f_{bulk}$ favors the creation of the ordered anisotropic phase, rather than the low-ordered (or isotropic) material required for the formation of disclination lines. Thus, $f_{bulk}$ is associated with the energy penalty required for the formation of disclination lines, which contain regions fluid with low order. When $a(T-T_{iso})$ is large, $f_{bulk}$ dominates and only the cholesteric is observed. However, in cholesterics with a very short pitch (large $q_0$), small values of $a(T-T_{iso})$ allow the elastic term $f_{el}$ to dominate and lead to the formation of the double twist structures characteristics of the BPs. Therefore, $f_{bulk}$ represents the energy barrier that the elastic term, $f_{el}$, must overcome to create the disclination lines that permit the material to accommodate the double twist cylinders of the BP.

Our results demonstrate that the main effect of the ternary compounds on the free energy of the LC is to affect the temperature at which the order-disorder transition occurs ($T_{iso}$). By decreasing $T_{iso}$, the addition of pyrene to the BP-forming LC lowers the energy for the creation of defect cores; the addition of RM257 increases this energy penalty. In the other hand, since the pitch of the cholesteric does not change significantly with the increasing concentration of pyrene, RM257 or toluene, it is reasonable to assume that the elastic contribution to the free energy, $f_{el}$, does not change significantly by the addition of ternary compounds to the cholesteric LC.

The conclusions presented above help us understand the toluene-induced phase transitions presented in the previous section. Because toluene more closely resembles the chemical structure of pyrene than the other compounds studied here (RM257, 5CB and PS), we conclude that the effect of toluene on phase behavior of BPs is similar to the effect of pyrene. Thus, we hypothesize that, at room temperature, the addition of toluene leads to a decrease in the clearing point temperature ($T_{iso}$) of the BP-forming LC but does not partition preferentially into defects. Since $T_{iso}$ is directly related to $f_{bulk}$, the energy difference between ordered and disordered (isotropic) phases of the material, a lower value of $T_{iso}$ translates into a lower energy barrier for the creation of low order material found in disclination cores at room temperature. Once this energy barrier becomes low enough, after a sufficient amount of toluene has dissolved in the LC, the material creates the disclination cores required to accommodate double twist cylinders favored by $f_{el}$.

Pyrene as a "Sensitizer" for Response of BPs to Toluene.

Figures 29A, 29B:
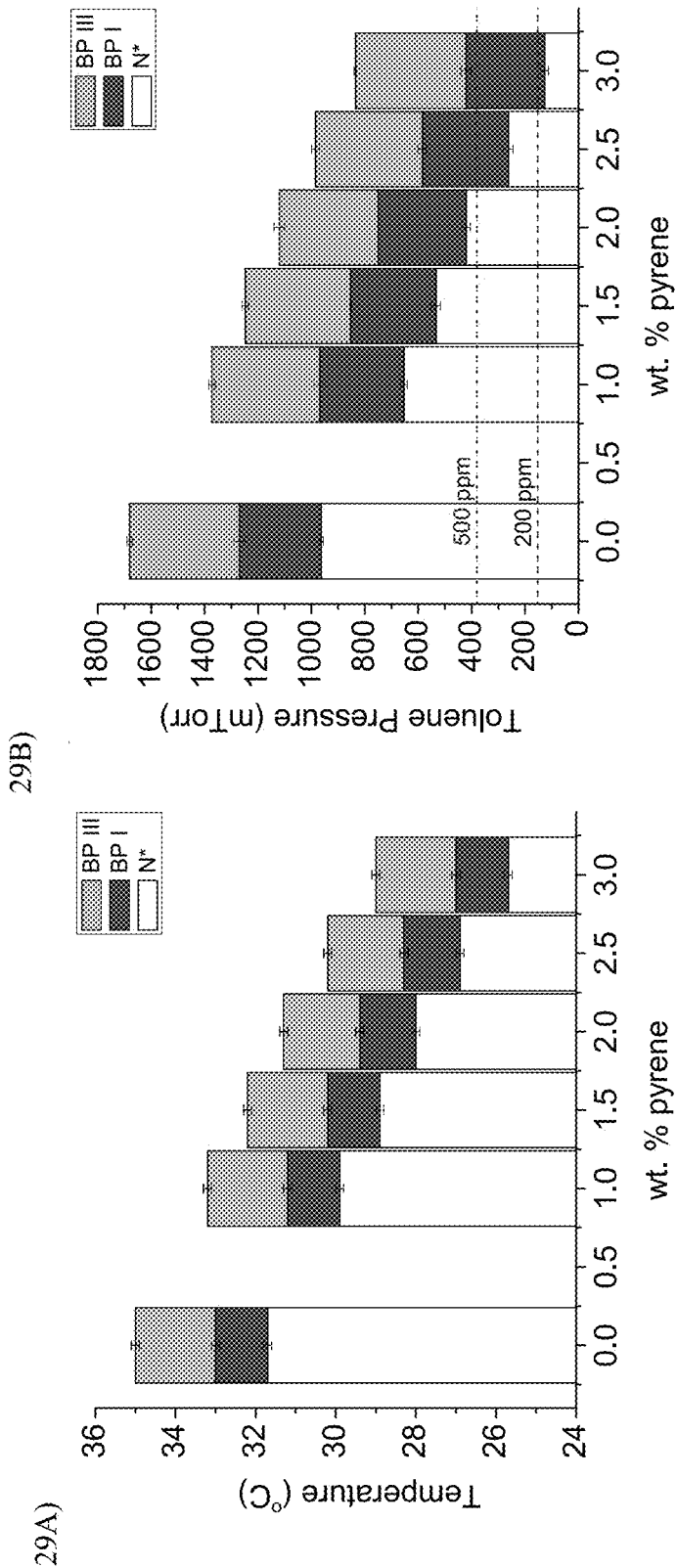
FIGS. 29A-29B. (29A) Addition of pyrene to the BP-forming LC (43.5 wt. % chiral dopant) led to a decrease in the N*-to-BP I transition temperature. As shown in (29B), the sensitivity to toluene also increases monotonically with pyrene concentration. The samples were exposed to toluene at 24° C.

With an understanding of the mechanism for toluene-driven phase transitions in BP-forming LCs, we proceeded to design a cholesteric material that responded sensitively to toluene. Using a cholesteric with 43.5 wt. % of the chiral dopant mixed with different concentrations of pyrene, we observed a monotonic decrease in the N*-to-BP I transition temperature (FIG. 29A). The other phase transition temperatures also shifted monotonically to lower temperatures with increasing concentrations of pyrene. The temperature range at which the BP was observed is 3.4° C. for all mixtures. As presented in FIG. 29B, the pyrene-containing LCs also exhibited increased sensitivity to toluene as the concentration of pyrene increase in the BP-forming mixture. While the mixture without pyrene required 980 mTorr of toluene to transition from the N* to the BP I, a mixture with 2.5 wt % pyrene only requires 280 mTorr of toluene. At atmospheric conditions (760 Torr), the equivalent concentration of 280 mTorr of toluene is 370 ppm, which is well below the 500 ppm 10-minute exposure limit for humans set by the OSHA. For a sample with 3.0 wt. % of toluene, the sample responded at 130 mTorr or 170 ppm of toluene, which is below the more stringent limit (200 ppm) for exposure over a period of 8 hours.[21]

We also investigated the effect of polystyrene (PS) additives on the phase behavior and toluene sensitivity of a BP-forming LC containing 43.5 wt. % of S-811. We observed that the addition of 1 wt. % and 2 wt. % of PS to the LC mixture led to an increase in the temperature range of the BP (see FIG. 30A) at lower temperatures, consistent with previous reports.[11] The mixture without PS had a cholesteric to BP I transition temperature at 31.9° C., a BP I to BP III transition temperature at 33.2° C., and a clearing point temperature at 35.3° C. The temperature range for this sample was 3.4° C. In contrast, the temperature range for the mixture containing 1 wt. % and 2 wt. % of PS had temperature ranges of 4.8° C. and 6° C., respectively. The cholesteric to BP I transition temperature was 27.5° C. and 25.2° C. for the samples containing 1 wt. % and 2 wt. % of PS, respectively.

Figures 30A, 30B:
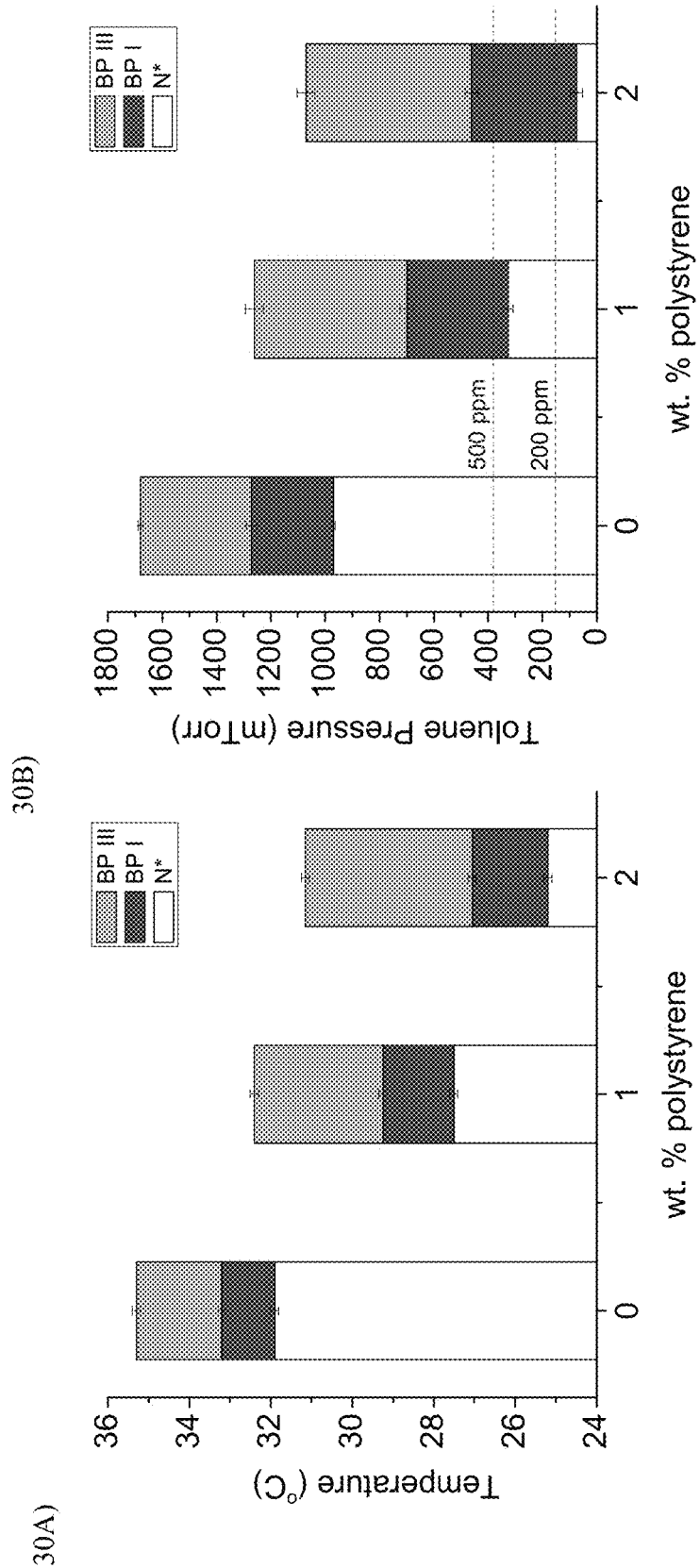
FIGS. 30A-30B. (30A) Phase transition temperatures of BP-forming LC (43.5 wt. % of chiral dopant) containing polystyrene. (30B) Pressures of toluene required to induce phase transitions in BP-forming LC (43.5 wt. % of chiral dopant) containing polystyrene. The samples were exposed to toluene at 24° C.

The sensitivity of the BP towards toluene was enhanced by the presence of PS in the LC mixture (see FIG. 30B). The mixture containing 1 wt. % of PS required 320 mTorr (430 ppm) to transition into the BP I while the mixture containing 2 wt. % of PS transition to BP I at only 75 mTorr (100 ppm).

This level of sensitivity towards toluene demonstrate that these materials could be used to detect toluene at concentrations that are relevant in occupational health settings.

Response to Other VOCs.

The N*-to-BP transition was also observed in the presence of other solvent vapors that occur as VOCs such as such as isooctane (gasoline), dichloromethane (paint strippers), ethanol (personal care products), etc. Different classes of compounds were tested: aromatics (toluene, styrene, o-xylene), primary alcohols (1-butanol, ethanol), nitriles (acetonitrile), chlorinated hydrocarbons (dichloromethane) and alkanes (isooctane).

In Table 1 of Example 1, we presented the results for the relative sensitivity of BP-forming LC to different VOCs. Cholesteric samples with 45 wt % S-811 were used and the pressure of solvent required to induce the N*-BP I transition was recorded. For each component, this pressure value was divided by the pressure of toluene required to induce the N*-BP 1 phase transition in the sample (720 mTorr). For example, a cholesteric sample exposed to styrene transitioned into BP 1 at 875 mTorr of styrene. The relative partitioning of styrene into the LC was calculated as 1.2, with respect to toluene. We found that those solvent molecules with aromatic moieties induced a response in the cholesteric LC at lower pressures than other types of compounds. We hypothesize that the relative selectivity towards aromatic compounds, and in particular to toluene, might be due to n-stacking interactions with the aromatic groups of the LC.[22,23] Finally, we note that the system did not respond to water vapor. This result indicates that devices based on solvent-induced phase transitions of BPs might not be adversely affected by changes in ambient humidity, a common problem for other LC-based sensing devices.

Conclusion.

In conclusion, in this example we characterized the phase behavior of BP-forming LC mixtures containing commercially available components S-811 and MLC 2142. Furthermore, we demonstrate that these BP-forming LCs are able to undergo several phase transitions into BPs at room temperature when exposed to vapors of toluene. By studying the phase behavior of BP-forming LCs containing other non-volatile compounds, we concluded that the effect of toluene is to reduce the energy penalty associated with the creation of disclination lines.

Our results indicate that toluene does not change the cholesteric pitch significantly, indicating that the changes in elastic energy of the LC are small with the addition of toluene. Also, based on the effect of pyrene on the phase behavior of the BPs, which imitates the effect toluene, we conclude that toluene does not appear to partition preferentially into the defects. Moreover, we learned that the chemical identity of the ternary compound determines its effect on the phase behavior of the BP-forming LCs.

Our work has technological relevance in the area of chemical sensing of toluene and other VOCs. By pre-loading a BP-forming LC with pyrene, we demonstrate that these materials can be used for high-sensitivity detection of aromatic VOC. To our knowledge, this is the first study to utilize BPs in chemical sensing applications. Our results also demonstrate that the lattice spacing of BP I is sensitivity to toluene vapors. We could exploit this effect to create high sensitivity optical elements that continually monitor the BP I Bragg reflection to create sensors for aromatic VOCs.

REFERENCES CITED 1. de Gennes, P. G. and J. Prost, *The Physics of Liquid Crystals*. 2nd Edition ed. International Series of Monographs on Physics 1995: Oxford University Press.
2. Yang, D. K. and P. P. Crooker, *Chiral-racemic phase diagrams of blue-phase liquid crystals*. Physical Review A, 1987. 35(10): p. 4419-4423.
3. Grebel, H., R. M. Hornreich, and S. Shtrikman, *Landau theory of cholesteric blue phases: The role of higher harmonics*. Physical Review A, 1984. 30(6): p. 3264-3278.
4. Hornreich, R. M. and S. Shtrikman, *Theory of light scattering in cholesteric blue phases*. Physical Review A, 1983. 28(3): p. 1791-1807.
5. Henrich, O., et al., *Structure of blue phase III of cholesteric liquid crystals*. Phys Rev Lett, 2011. 106(10): p. 107801.
6. Meiboom, S., M. Sammon, and W. Brinkman, *Lattice of disclinations: The structure of the blue phases of cholesteric liquid crystals*. Physical Review A, 1983. 27(1): p. 438-454.
7. Kikuchi, H., et al., *Polymer-stabilized liquid crystal blue phases*. Nat Mater, 2002. 1(1): p. 64-8.
8. Iwata, T., et al., *Control of Cross-Linking Polymerization Kinetics and Polymer Aggregated Structure in Polymer-Stabilized Liquid Crystalline Blue Phases*. Macromolecules, 2009. 42(6): p. 2002-2008.
9. Karatairi, E., et al., *Nanoparticle-induced widening of the temperature range of liquid-crystalline blue phases*. Physical Review E, 2010. 81(4).
10. Ravnik, M., et al., *Three-dimensional colloidal crystals in liquid crystalline blue phases*. Proc Natl Acad Sci USA, 2011. 108(13): p. 5188-92.
11. Kasch, N., I. Dierking, and M. Turner, *Stabilization of the liquid crystalline blue phase by the addition of short-chain polystyrene*. Soft Matter, 2013. 9(19): p. 4789-4793.
12. Dickert, F. L., A. Haunschild, and P. Hofmann, *Cholesteric Liquid-Crystals for Solvent Vapor Detection—Elimination of Cross-Sensitivity by Band Shape-Analysis and Pattern-Recognition*. Fresenius Journal of Analytical Chemistry, 1994. 350(10-11): p. 577-581.
13. Winterbottom, D. A., R. Narayanaswamy, and I. M. Raimundo, *Cholesteric liquid crystals for detection of organic vapours*. Sensors and Actuators B: Chemical, 2003. 90(1-3): p. 52-57.
14. Chang, C.-K., et al., *Optical detection of organic vapors using cholesteric liquid crystals*. Applied Physics Letters, 2011. 99(7): p. 073504.
15. Chang, C.-K., et al., *Cholesteric liquid crystal-carbon nanotube hybrid architectures for gas detection*. Applied Physics Letters, 2012. 100(4): p. 043501.
16. Berreman, D. W. and T. J. Scheffer, *Bragg Reflection of Light from Single-Domain Cholesteric Liquid-Crystal Films*. Physical Review Letters, 1970. 25(9): p. 577-581.
17. Shim, K. S., et al., *Temperature-independent pitch invariance in cholesteric liquid crystal*. Opt Express, 2014. 22(13): p. 15467-72.
18. Meiboom, S. and M. Sammon, *Structure of the Blue Phase of a Cholesteric Liquid Crystal*. Physical Review Letters, 1980. 44(13): p. 882-885.
19. Cladis, P. E., P. Pieranski, and M. Joanicot, *Elasticity of Blue Phase-I of Cholesteric Liquid-Crystals*. Physical Review Letters, 1984. 52(7): p. 542-545.

20. Wright, D. C. and N. D. Mermin, *Crystalline liquids: the blue phases.* Reviews of Modern Physics, 1989. 61(2): p. 385-432.
21. *OSHA InfoSheet: Toluene Safety in the Workplace.* 2013, U.S. Department of Labor, Occupational Health & Safety Administration: Washington, D.C.
22. Hunter, C. A. and J. K. M. Sanders, *The Nature of Pi-Pi Interactions.* Journal of the American Chemical Society, 1990. 112(14): p. 5525-5534.
23. Tsuzuki, S., et al., *Origin of Attraction and Directionality of the π/π Interaction: Model Chemistry Calculations of Benzene Dimer Interaction.* Journal of the American Chemical Society, 2002. 124(1): p. 104-112.

Those skilled in the art will recognize, or be able to ascertain using no more than routine experimentation, numerous equivalents to the specific materials and methods described herein. Such equivalents are considered to be within the scope of this invention and encompassed by the following claims.

What is claimed is:

1. A blue phase-forming liquid crystal composition for detecting a target analyte in a sample, comprising a nematic liquid crystal, a chiral dopant, and a non-volatile organic compound that increases the sensitivity of response of the blue phase-forming liquid crystal composition to the target analyte, wherein the weight % of chiral dopant in the composition is from 20% to 60%.

2. The composition of claim 1, wherein the chiral dopant is selected from the group consisting of S-811 ((S)-Octan-2-yl 4-((4-(hexyloxy)benzoyl)oxy)benzoate), R-811 ((R)-Octan-2-yl 4-((4-(hexyloxy)benzoyl)oxy)benzoate),

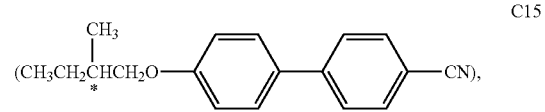

CB 15 ((S)-4-(2-methylbutyl)-4-cyanobiphenyl), S-1011, R-1011, S-2011, and R-2011.

3. The composition of claim 1, wherein the non-volatile organic compound is:
   (a) a polymer or a polycyclic aromatic compound; or
   (b) selected from the group consisting of pyrene, phenanthrene, polystyrene, benzoic acid, biphenyl, a halogenated biphenyl, and benzopyrene.

4. An array-based device for detecting and/or quantifying a target analyte in a sample, comprising a plurality of blue phase-forming liquid crystal compositions of claim 1.

* * * * *